US008470758B2

(12) United States Patent
Amin et al.

(10) Patent No.: US 8,470,758 B2
(45) Date of Patent: Jun. 25, 2013

(54) DETERGENT COMPOSITIONS AND METHODS OF USE FOR AN ALPHA-AMYLASE POLYPEPTIDE OF *BACILLUS* SPECIES 195

(75) Inventors: Neelam S. Amin, Palo Alto, CA (US); Melodie Estabrook, Mountain View, CA (US); Brian E. Jones, Leidschendam (NL); Marc Kolkman, Oegstgeest (NL); Casper Vroemen, Oegstgeest (NL); Walter Weyler, San Francisco, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 13/312,555

(22) Filed: Dec. 6, 2011

(65) Prior Publication Data

US 2012/0142074 A1 Jun. 7, 2012

Related U.S. Application Data

(63) Continuation of application No. 12/519,879, filed as application No. PCT/US2007/024959 on Dec. 6, 2007, now Pat. No. 8,097,444.

(60) Provisional application No. 60/876,241, filed on Dec. 21, 2006, provisional application No. 60/880,236, filed on Jan. 12, 2007.

(51) Int. Cl.
*C12N 9/00* (2006.01)
*C12N 9/24* (2006.01)
*C12N 1/20* (2006.01)
*C12N 15/00* (2006.01)
*C11D 3/386* (2006.01)
*C11D 3/00* (2006.01)
*C07H 21/04* (2006.01)

(52) U.S. Cl.
USPC ........ 510/392; 435/183; 435/200; 435/252.3; 435/320.1; 510/226; 536/23.2

(58) Field of Classification Search
None
See application file for complete search history.

(56) References Cited

U.S. PATENT DOCUMENTS

| | | | |
|---|---|---|---|
| 4,106,991 A | 8/1978 | Markussen et al. | |
| 4,435,307 A | 3/1984 | Barbesgaard et al. | |
| 4,661,452 A | 4/1987 | Markussen et al. | |
| 5,281,526 A | 1/1994 | Good et al. | |
| 5,457,046 A | 10/1995 | Woldike et al. | |
| 5,648,263 A | 7/1997 | Schulein et al. | |
| 5,686,593 A | 11/1997 | Woldike et al. | |
| 5,691,178 A | 11/1997 | Schulein et al. | |
| 5,763,254 A | 6/1998 | Woldike et al. | |
| 5,763,385 A * | 6/1998 | Bott et al. ............ | 510/392 |
| 5,776,757 A | 7/1998 | Schulein et al. | |
| 5,871,550 A | 2/1999 | Goedegebuur et al. | |
| 6,562,612 B2 | 5/2003 | Jones et al. | |
| 7,122,334 B2 | 10/2006 | Schellenberger et al. | |
| 7,413,877 B2 | 8/2008 | Collier et al. | |
| 2006/0014265 A1 | 1/2006 | Ferrari et al. | |
| 2010/0035787 A1 | 2/2010 | Amin et al. | |

FOREIGN PATENT DOCUMENTS

| | | |
|---|---|---|
| EP | 0 218 272 A1 | 4/1987 |
| EP | 0 238 023 A2 | 9/1987 |
| EP | 0 238 216 A1 | 9/1987 |
| EP | 0 258 068 A2 | 3/1988 |
| EP | 0 260 105 A2 | 3/1988 |
| EP | 0 305 216 A1 | 3/1989 |
| EP | 0 331 376 A2 | 9/1989 |
| EP | 0 407 225 A1 | 1/1991 |
| EP | 0 495 257 A1 | 7/1992 |
| GB | 1372034 A | 10/1974 |
| GB | 1483591 A | 8/1977 |
| JP | 64/074992 A | 3/1989 |
| WO | WO 89/06270 A1 | 7/1989 |
| WO | WO 89/06279 A1 | 7/1989 |
| WO | WO 89/09259 A1 | 10/1989 |
| WO | WO 91/16422 A1 | 10/1991 |
| WO | WO 92/05249 A1 | 4/1992 |
| WO | WO 92/19708 A1 | 11/1992 |
| WO | WO 92/19709 A1 | 11/1992 |
| WO | WO 92/19729 A1 | 11/1992 |
| WO | WO 91/17243 A1 | 3/1993 |
| WO | WO 91/17244 A1 | 3/1993 |
| WO | WO 93/24618 A1 | 12/1993 |
| WO | WO 94/01541 A1 | 1/1994 |
| WO | WO 94/07998 A1 | 4/1994 |
| WO | WO 94/25578 A1 | 11/1994 |
| WO | WO 94/25583 A1 | 11/1994 |
| WO | WO 95/06720 A1 | 3/1995 |
| WO | WO 95/10602 A1 | 4/1995 |
| WO | WO 95/14783 A1 | 6/1995 |
| WO | WO 95/22615 A1 | 8/1995 |
| WO | WO 95/24471 A1 | 9/1995 |
| WO | WO 95/30744 A2 | 11/1995 |
| WO | WO 95/35381 A1 | 12/1995 |

(Continued)

OTHER PUBLICATIONS

Accession O24781. Jan. 1, 1998.*
GenBank Accession No. BAA22082.1, "Alpha-amylase [*Bacillus* sp.]," accessed at http://www.ncbi.nlm.nih.gov/protein/BAA22082 on Oct. 3, 2012, 2 pp.
Wei et al. "Secreted Expression of Synthesized Hyperthermophilic alpha-Amylase Gene PFA in *Pichia pastoris*," *J. Chinese Biotechnology* 25(1):65-69. (Abstract only in English).
Accession No. O24781. Jan. 1, 1998.
*Cayot, P. et al. "The Quantification of Protein Amino Groups by the Trinitrobenzenesulfonic Acid Method: A Reexamination." *Analytical Biochemistry* 249(2):184-200, 1997.
*Conti, M. et al. "Capillary isoelectric focusing: the problem of protein solubility." *Journal of Chromatography A* 757(1-2):237-245, 1997.

(Continued)

*Primary Examiner* — Christian Fronda
(74) *Attorney, Agent, or Firm* — Danisco US Inc.

(57) ABSTRACT

Disclosed herein are compositions comprising an alpha-amylase enzyme obtained from *Bacillus* sp. no. 195, and methods of using the enzyme to clean surfaces and textiles. Also disclosed are variants of the enzyme with different signal sequences.

1 Claim, 11 Drawing Sheets

FOREIGN PATENT DOCUMENTS

| WO | WO 96/00292 A1 | 1/1996 |
|---|---|---|
| WO | WO 96/11262 A1 | 4/1996 |
| WO | WO 96/12012 A1 | 4/1996 |
| WO | WO 96/13580 A1 | 5/1996 |
| WO | WO 96/27002 A1 | 9/1996 |
| WO | WO 96/29397 A1 | 9/1996 |
| WO | WO 96/39528 A | 12/1996 |
| WO | WO 97/04079 A1 | 2/1997 |
| WO | WO 97/07202 A1 | 2/1997 |
| WO | WO 98/08940 A1 | 3/1998 |
| WO | WO 98/12307 A1 | 3/1998 |
| WO | WO 98/15257 A1 | 4/1998 |
| WO | WO 98/20115 A1 | 5/1998 |
| WO | WO 98/20116 A1 | 5/1998 |
| WO | WO 98/34946 A1 | 8/1998 |
| WO | WO 99/01544 A1 | 1/1999 |
| WO | WO 00/29560 A1 | 5/2000 |
| WO | WO 01/14629 A1 | 3/2001 |
| WO | WO 01/34899 A1 | 5/2001 |
| WO | WO 02/31124 | 4/2002 |
| WO | WO2005/056783 A1 | 6/2005 |

OTHER PUBLICATIONS

*Dartois, V. et al. "Cloning, nucleotide sequence and expression in *Escherichia coli* of a lipase gene from *Bacillus subtilis* 168." *Biochimica et Biophysica Acta* 1131(3):253-260, 1992.

*Database GenBank. "*Bacillus* sp. DNA for alpha-amylase, complete cds." Accession No. AB006823, 2000.

*Hage, R. et al. "Efficient manganese catalysts for low-temperature bleaching." *Nature* 369(6482):637-639, 1994.

*Ito, S. et al. "Alkaline detergent enzymes from alkaliphiles: enzymatic properties, genetics, and structures." *Extremophiles* 2(3):185-190, 1998.

*Kaushik, J.K. et al. "Why Is Trehalose an Exceptional Protein Stabilizer?: An analysis of the thermal stability of proteins in the presence of the compatible osmolyte trehalose." *J. Biol. Chem.* 278(29):26458-26465, 2003.

*Kawaguchi, T. et al. "Purification and some properties of a Haim-sensitive alpha-amylase from newly isolated *Bacillus* sp. No. 195." *Bioscience, Biotechnology, and Biochemistry* 56(11):1792-1796, 1992.

*Lo, H.-F. et al. "Deletion analysis of the C-terminal region of the a-amylase of *Bacillus* sp. strain TS-23." *Archives of Microbiology* 178(2):115-123, 2002.

*Marco, J.L. et al. "Purification and characterization of a truncated*Bacillus subtilis* α-amylase produced by*Escherichia coli*." *Applied Microbiology and Biotechnology* 44(6):746-752, 1996.

*Morris, M.A. et al. "The Effect of Wash Temperature on Removal of Particulate and Oily Soil from Fabrics of Varying Fiber Content." *Textile Research Journal* 52(4):280-286, 1982.

*Sumitani, J. et al. "New type of starch-binding domain: the direct repeat motif in the C-terminal region of *Bacillus* sp. No. 195 alpha-amylase contributes to starch binding and raw starch degrading." *The Biochemical Journal* 350 Pt 2:477-484, 2000.

*Vihinen, M. et al. "C-terminal truncations of a thermostable *Bacillus stearothermophilus* α-amylase." *Protein Eng.* 7(10):1255-1259, 1994.

* cited by examiner

FIGURE 1A

```
   1 atgccagccc tctaccaggg cgtcattgcc gacgtccgag caaagagaaa acgcttgcaa
  61 gttttggcca agatggtcct catcgccctc cttggcacgc tgctttcggc caccgctttc
 121 gccgccccgg cgagcgccgc agcccccggc cccaaggacg ccaccgccgt catgttctcc
 181 tggacatgga acgcgatcgc ccgtgaatgc accgagaacc tcggccccgc cggctacggc
 241 tacgtgcaga cctcgcctcc ccaggaacac atccaaggcg ccgcgtggtg gacccattac
 301 cagcccgtca gctacaagat cgagtcccgc ttcggcaccc gggcggagtt caaggccatg
 361 gtggacacct gccacgccgc aggcgtgaag gtgatcgcgg acgccgtcat caaccacatg
 421 accggccaga gcgccggcgg caccggctgg gccggttcca ccttccagca ctacgactac
 481 ccgggcatct accagtccca ggacttccac tcctgccgcc gcaacatcgc caactaccag
 541 gaccgctggg aggtacagga gtgcaacctc gtgaacctcg cggacctgaa cacttcctcg
 601 tcctacgtcc aaggaaagat tgcggcatac ctgaacgatc tcgtctcgct cggcgtcgac
 661 ggcctccgca ttgacgccgt caagcacatc gcggcgagcg acatgcaggg catcctgtcc
 721 aaggtgaacg accgcgcccg cctctacatc gtccaggaag tcatccgcgc caacgagccc
 781 atccagcccg aggaatacac cagcaacggt gacatccacg agttcgcctt cgcccgtaag
 841 ctcaaggaag ccttcaacgg cggcaccatc aactggctga ccaccggcaa cggaatcggc
 901 cccacctggg ccggcttcct gccgaacgcc aacgccgcag tgttcgtgga caaccacgac
 961 accgagcgca acgtgaaaac cctcacctac aaggacggag ccaactacga cctcgcccag
1021 atcttcaccc tcgcctggaa ctacggctcg ccgtccatcc actcgggcta ttccttctcg
1081 aacaacgacg ccggcccggc actcgccgga acggcgaagt gattgatcc ggtatgcggc
1141 cagaacggct ggacctgcaa gcacgcccag acgggcatcg agaacatggt gggcttccgc
1201 acccagacgt acggcaccgc cgtcgtgaac aaatgggaca acggctccag cgccatcgcg
1261 ttcgccgggg gagacaaggg ctacgtggcg ataaaccgcg gcagcgccct caccgcacc
1321 ttccagacct ccctgcccgc gggcaactac tgcaacgtga tcgtcggcct gcccaactcc
1381 accggctgct cggccggcgg cgtggtgacg gttgacgccg cgggcacctt cacggccacc
1441 gtggaccaga actccgcgtt cgcactgcac gtcggcgcga aggccggaac gcagcagccc
1501 ggaccgggcg cgggcgacat gaaggtgtac tactcgacgt cgaagggctg gagcgactac
```

FIGURE 1B

```
1561 aagatccact accgcgtggg taccggcgcc tggaccaccg ctcccggtgc cggcatgacg 1621 gccgcctgcg ccggctgggt ctcgtacacc gtcccggccg gctccaccgg agccaccgcc 1681 gccttcaaca acggcagcgg cacctgggac aacaacaaca ccagcaacta cgcactcagc 1741 ggcgcggtca gcacagtgaa cggcggcgtc gtggggcata cggacccctg caccgaaagc 1801 gcgcccgccc cggccgacac agccgtggtg ttctactcca ccaacaaggg ctggtccgcc 1861 tacaacatcc actaccgcgt gggtacgggc gcctggacca ccgcgccggg cagcgccatg 1921 acggccgcgt gcaccggctg gatgaccgcc tccatccccc tgggcggagc ctccggaatc 1981 accgctgcct tcaacaatgg cgcgggcacc tgggataaca acgccggcgc cgattacagc 2041 gttggcagcg gttaccggca ggtgaaggac ggcgtggtca gcacgggaaa cccctgcgcc 2101 tga
```

FIGURE 2 atgaaacaacaaaaacggctttacgcccgattgctgacgctgttatttgcgctcatcttcttgctgcctcattctgcagcttcagcagcagc
accgggaccgaaagatgctacagcggtcatgtttagctggacgtggaatgccattgccagagaatgcacggaaaatcttggcccggca
ggctatggatatgtccaaacgtcaccgccgcaagaacatattcaaggcgccgcttggtggacacattatcagccggtcagctataaaatc
gaaagccgctttggcacacgggcagaatttaaagcgatggtcgacacatgccatgctgctggagtcaaagtcatcgccgatgccgtcat
caatcatatgacaggccaatcagcaggcggaacaggatgggcaggaagcacgtttcagcattatgactatccgggcatctatcagagc
caggactttcatagctgccggagaaacatcgccaactatcaggatagatgggaagtccaagaatgcaacctggtcaatctggcggatct
gaatacgagcagcagctatgtccaaggaaaaatcgccgcctatctgaatgatctggtcagccttggagtcgatggactgagaatcgatg
ccgtcaaacatatcgccgccagcgatatgcaaggaatcctgagcaaagtcaacgatagagcccgcctgtatatcgtccaagaagtcatc
agagcgaacgaaccgattcagccggaagaatatacgagcaacggcgacatccatgaatttgcctttgcccggaaactgaaagaagcg
tttaacggcggcacaatcaattggctgacgacgggaaatggaattggaccgacatgggcaggatttctgccgaatgccaatgctgctgt
ctttgtcgataaccatgacacggaaagaaatggcgaaacgctgacgtataaagacggcgccaattatgacctggcccagatctttacact
ggcgtggaattatggaagcccgagcatccatagcggatatagctttagcaacaacgatgctggaccggcattggcaggaaatggcgaa
gtcatcgatccggtctgcggacaaaatggctggacatgcaaacatgcccaaacgggcatcgaaaacatggtcggcttcggacacaaa
catatggaacggcggtcgttaataaatgggataacggcagcagcgctatcgcttttggcagaggcgataaaggatatgtcgccatcaat
agaggaagcgccctgacgagaacgtttcaaacaagccttccggcaggcaattattgcaatgtcatcgtcggactgccgaatagcacag
gatgcagcgcaggaggagtcgttacagttgacgccgctggaacatttacagcgacggtcgatcaaaatagcgcctttgccttcatgttg
gagcgaaagcgggaacacaacaaccgggaccgggagcaggagatatgaaagtctattatagcacgagcaaaggatggtccgactac
aaaatccattatcgggtcggaacaggagcatggacaacagcacctggagctggaatgacagcagcatgcgcaggatgggtctcatata
cagttccggcgggatcaacaggagcaacagcggcgttcaataatggcagcggcacgtgggataacaacaacacgagcaactatgctc
ttagcggagcagtcagcacagttaatggaggagtcgtcggacatacagatccgtgcacagaatcagcaccggcaccggcagatacag
cagtcgtcttttattcaacgaacaaaggctggtcagcgtataacattcattatagagtcggcacaggcgcttggacgacggctccgggat
cagcaatgacagcggcttgcacaggctggatgacagcatcaattccgcttggaggagcatcaggaatcacggcggcgtttaacaacg
gagcaggaacatgggataataacgccggagcggattattcagtcggcagcggctatagacaagtcaaagatggcgtcgtcagcacag
gcaatccgtgcgcatga

FIGURE 3

```
  1 mpalyqgvia dvrakrkrlq vlakmvlial lgtllsataf aapasaaapg pkdatavmfs
 61 wtwnaiarec tenlgpagyg yvqtsppqeh iqgaawwthy qpvsykiesr fgtraefkam
121 vdtchaagvk viadavinhm tgqsaggtgw agstfqhydy pgiyqsqdfh scrrnianyq
181 drwevqecnl vnladlntss syvqgkiaay lndlvslgvd glridavkhi aasdmqgils
241 kvndrarlyi vqeviranep iqpeeytsng dihefafark lkeafnggti nwlttgngig
301 ptwagflpna naavfvdnhd terngetlty kdganydlaq iftlawnygs psihsgysfs
361 nndagpalag ngevidpvcg qngwtckhaq tgienmvgfr tqtygtavvn kwdngssaia
421 fgrgdkgyva inrgsaltrt fqtslpagny cnvivglpns tgcsaggvvt vdaagtftat
481 vdqnsafalh vgakagtqqp gpgagdmkvy ystskgwsdy kihyrvgtga wttapgagmt
541 aacagwvsyt vpagstgata afnngsgtwd nnntsnyals gavstvnggv vghtdpctes
601 apapadtavv fystnkgwsa ynihyrvgtg awttapgsam taactgwmta siplggasgi
661 taafnngagt wdnnagadys vgsgyrqvkd gvvstgnpca
```

FIGURE 4

```
  1 mkqqkrlyar lltllfalif llphsaasaA APGPKDATAV MFSWTWNAIA RECTENLGPA
 61 GYGYVQTSPP QEHIQGAAWW THYQPVSYKI ESRFGTRAEF KAMVDTCHAA GVKVIADAVI
121 NHMTGQSAGG TGWAGSTFQH YDYPGIYQSQ DFHSCRRNIA NYQDRWEVQE CNLVNLADLN
181 TSSSYVQGKI AAYLNDLVSL GVDGLRIDAV KHIAASDMQG ILSKVNDRAR LYIVQEVIRA
241 NEPIQPEEYT SNGDIHEFAF ARKLKEAFNG GTINWLTTGN GIGPTWAGFL PNANAAVFVD
301 NHDTERNGET LTYKDGANYD LAQIFTLAWN YGSPSIHSGY SFSNNDAGPA LAGNGEVIDP
361 VCGQNGWTCK HAQTGIENMV GFRTQTYGTA VVNKWDNGSS AIAFGRGDKG YVAINRGSAL
421 TRTFQTSLPA GNYCNVIVGL PNSTGCSAGG VVTVDAAGTF TATVDQNSAF ALHVGAKAGT
481 QQPGPGAGDM KVyystskgw sdykihyrvg tgawttapga gmtaacagwv sytvpagstg
541 ataafnngsg twdnnntsny alsgavstvn ggvvghtdpc tesapapadt avvfystnkg
601 wsaynihyrv gtgawttapg samtaactgw mtasiplgga sgitaafnng agtwdnnaga
661 dysvgsgyrq vkdgvvstgn pca
    (SEQ ID NO:4)
```

AmyNo195 nucleic acid - schematic
2190 bp

SEQUENCE LISTING

```
<160> NUMBER OF SEQ ID NOS: 5

<210> SEQ ID NO 1
<211> LENGTH: 2103
<212> TYPE: DNA
<213> ORGANISM: Bacillus sp.

<400> SEQUENCE: 1
atgccagccc tctaccaggg cgtcattgcc gacgtccgag caaagagaaa acgcttgcaa        60
gttttggcca agatggtcct catcgccctc cttggcacgc tgctttcggc caccgctttc       120
gccgccccgg cgagcgccgc agcccccggc cccaaggacg ccaccgccgt catgttctcc       180
tggacatgga acgcgatcgc ccgtgaatgc accgagaacc tcggccccgc cggctacggc       240
tacgtgcaga cctcgcctcc ccaggaacac atccaaggcg ccgcgtggtg gacccattac       300
cagcccgtca gctacaagat cgagtcccgc ttcggcaccc gggcggagtt caaggccatg       360
gtggacacct gccacgccgc aggcgtgaag gtgatcgcgg acgccgtcat caaccacatg       420
accggccaga gcgccggcgg caccggctgg gccggttcca ccttccagca ctacgactac       480
ccgggcatct accagtccca ggacttccac tcctgccgcc gcaacatcgc caactaccag       540
gaccgctggg aggtacagga gtgcaacctc gtgaacctcg cggacctgaa cacttcctcg       600
tcctacgtcc aaggaaagat tgcggcatac ctgaacgatc tcgtctcgct cggcgtcgac       660
ggcctccgca ttgacgccgt caagcacatc gcggcgagcg acatgcaggg catcctgtcc       720
aaggtgaacg accgcgcccg cctctacatc gtccaggaag tcatccgcgc caacgagccc       780
atccagcccg aggaatacac cagcaacggt gacatccacg agttcgcctt cgcccgtaag       840
ctcaaggaag ccttcaacgg cggcaccatc aactggctga ccaccggcaa cggaatcggc       900
cccacctggg ccggcttcct gccgaacgcc aacgccgcag tgttcgtgga caaccacgac       960
accgagcgca acggtgaaac cctcacctac aaggacggag ccaactacga cctcgcccag      1020
atcttcaccc tcgcctggaa ctacggctcg ccgtccatcc actcgggcta ttccttctcg      1080
aacaacgacg ccggcccggc actcgccgga aacggcgaag tgattgatcc ggtatgcggc      1140
cagaacggct ggacctgcaa gcacgcccag acgggcatcg agaacatggt gggcttccgc      1200
acccagacgt acggcaccgc cgtcgtgaac aaatgggaca acggctccag cgccatcgcg      1260
```

| | |
|---|---|
| ttcggccggg gagacaaggg ctacgtggcg ataaaccgcg gcagcgccct cacccgcacc | 1320 |
| ttccagacct ccctgcccgc gggcaactac tgcaacgtga tcgtcggcct gcccaactcc | 1380 |
| accggctgct cggccggcgg cgtggtgacg gttgacgccg cgggcacctt cacggccacc | 1440 |
| gtggaccaga actccgcgtt cgcactgcac gtcggcgcga aggccggaac gcagcagccc | 1500 |
| ggaccgggcg cgggcgacat gaaggtgtac tactcgacgt cgaagggctg gagcgactac | 1560 |
| aagatccact accgcgtggg taccggcgcc tggaccaccg ctcccggtgc cggcatgacg | 1620 |
| gccgcctgcg ccggctgggt ctcgtacacc gtcccggccg gctccaccgg agccaccgcc | 1680 |
| gccttcaaca acggcagcgg cacctgggac aacaacaaca ccagcaacta cgcactcagc | 1740 |
| ggcgcggtca gcacagtgaa cggcggcgtc gtggggcata cggacccctg caccgaaagc | 1800 |
| gcgcccgccc cggccgacac agccgtggtg ttctactcca ccaacaaggg ctggtccgcc | 1860 |
| tacaacatcc actaccgcgt gggtacgggc gcctggacca ccgcgccggg cagcgccatg | 1920 |
| acggccgcgt gcaccggctg gatgaccgcc tccatccccc tgggcggagc ctccggaatc | 1980 |
| accgctgcct tcaacaatgg cgcgggcacc tgggataaca acgccggcgc cgattacagc | 2040 |
| gttggcagcg gttaccggca ggtgaaggac ggcgtggtca gcacgggaaa cccctgcgcc | 2100 |
| tga | 2103 |

<210> SEQ ID NO 2
<211> LENGTH: 2052
<212> TYPE: DNA
<213> ORGANISM: Artificial
<220> FEATURE:
<223> OTHER INFORMATION: synthetic optimized coding sequence

<400> SEQUENCE: 2

| | |
|---|---|
| atgaaacaac aaaaacggct ttacgcccga ttgctgacgc tgttatttgc gctcatcttc | 60 |
| ttgctgcctc attctgcagc ttcagcagca gcaccgggac cgaaagatgc tacagcggtc | 120 |
| atgtttagct ggacgtggaa tgccattgcc agagaatgca cggaaaatct ggcccggca | 180 |
| ggctatggat atgtccaaac gtcaccgccg caagaacata ttcaaggcgc cgcttggtgg | 240 |
| acacattatc agccggtcag ctataaaatc gaaagccgct ttggcacacg gcagaatttt | 300 |
| aaagcgatgg tcgacacatg ccatgctgct ggagtcaaag tcatcgccga tgccgtcatc | 360 |
| aatcatatga caggccaatc agcaggcgga acaggatggg caggaagcac gtttcagcat | 420 |
| tatgactatc cgggcatcta tcagagccag gactttcata gctgccggag aaacatcgcc | 480 |
| aactatcagg atagatggga agtccaagaa tgcaacctgg tcaatctggc ggatctgaat | 540 |
| acgagcagca gctatgtcca aggaaaaatc gccgcctatc tgaatgatct ggtcagcctt | 600 |
| ggagtcgatg gactgagaat cgatgccgtc aaacatatcg ccgccagcga tatgcaagga | 660 |
| atcctgagca agtcaacgat agagcccgc ctgtatatcg tccaagaagt catcagagcg | 720 |
| aacgaaccga ttcagccgga agaatatacg agcaacggcg acatccatga atttgccttt | 780 |
| gcccggaaac tgaagaagc gtttaacggc ggcacaatca attggctgac gacggaaat | 840 |
| ggaattggac cgacatgggc aggatttctg ccgaatgcca atgctgctgt ctttgtcgat | 900 |
| aaccatgaca cggaaagaaa tggcgaaacg ctgacgtata agacggcgc caattatgac | 960 |
| ctggcccaga tctttacact ggcgtggaat tatggaagcc cgagcatcca tagcggatat | 1020 |
| agctttagca acaacgatgc tggaccggca ttggcaggaa atggcgaagt catcgatccg | 1080 |
| gtctgcggac aaaatggctg gacatgcaaa catgcccaaa cgggcatcga aacatggtc | 1140 |
| ggctttcgga cacaaacata tggaacggcg gtcgttaata aatgggataa cggcagcagc | 1200 |

```
gctatcgctt ttggcagagg cgataaagga tatgtcgcca tcaatagagg aagcgccctg   1260
acgagaacgt ttcaaacaag ccttccggca ggcaattatt gcaatgtcat cgtcggactg   1320
ccgaatagca caggatgcag cgcaggagga gtcgttacag ttgacgccgc tggaacattt   1380
acagcgacgg tcgatcaaaa tagcgccttt gcccttcatg ttggagcgaa agcgggaaca   1440
caacaaccgg gaccgggagc aggagatatg aaagtctatt atagcacgag caaggatgg    1500 tccgactaca aaatccatta tcgggtcgga acaggagcat ggacaacagc acctggagct   1560
ggaatgacag cagcatgcgc aggatgggtc tcatatacag ttccggcggg atcaacagga   1620 gcaacagcg cgttcaataa tggcagcggc acgtgggata caacaacac gagcaactat     1680 gctcttagcg gagcagtcag cacagttaat ggaggagtcg tcggacatac agatccgtgc   1740
acagaatcag caccggcacc ggcagataca gcagtcgtct tttattcaac gaacaaaggc   1800
tggtcagcgt ataacattca ttatagagtc ggcacaggcg cttggacgac ggctccggga   1860
tcagcaatga cagcggcttg cacaggctgg atgacagcat caattccgct tggaggagca   1920
tcaggaatca cggcggcgtt taacaacgga gcaggaacat gggataataa cgccggagcg   1980
gattattcag tcggcagcgg ctatagacaa gtcaaagatg gcgtcgtcag cacaggcaat   2040
ccgtgcgcat ga                                                      2052

<210> SEQ ID NO 3
<211> LENGTH: 700
<212> TYPE: PRT
<213> ORGANISM: Bacillus sp.

<400> SEQUENCE: 3

Met Pro Ala Leu Tyr Gln Gly Val Ile Ala Asp Val Arg Ala Lys Arg
1               5                   10                  15

Lys Arg Leu Gln Val Leu Ala Lys Met Val Leu Ile Ala Leu Leu Gly
            20                  25                  30

Thr Leu Leu Ser Ala Thr Ala Phe Ala Ala Pro Ala Ser Ala Ala Ala
        35                  40                  45

Pro Gly Pro Lys Asp Ala Thr Ala Val Met Phe Ser Trp Thr Trp Asn
    50                  55                  60

Ala Ile Ala Arg Glu Cys Thr Glu Asn Leu Gly Pro Ala Gly Tyr Gly
65                  70                  75                  80

Tyr Val Gln Thr Ser Pro Pro Gln Glu His Ile Gln Gly Ala Ala Trp
                85                  90                  95

Trp Thr His Tyr Gln Pro Val Ser Tyr Lys Ile Glu Ser Arg Phe Gly
            100                 105                 110

Thr Arg Ala Glu Phe Lys Ala Met Val Asp Thr Cys His Ala Ala Gly
        115                 120                 125

Val Lys Val Ile Ala Asp Ala Val Ile Asn His Met Thr Gly Gln Ser
    130                 135                 140

Ala Gly Gly Thr Gly Trp Ala Gly Ser Thr Phe Gln His Tyr Asp Tyr
145                 150                 155                 160

Pro Gly Ile Tyr Gln Ser Gln Asp Phe His Ser Cys Arg Arg Asn Ile
                165                 170                 175

Ala Asn Tyr Gln Asp Arg Trp Glu Val Gln Glu Cys Asn Leu Val Asn
            180                 185                 190

Leu Ala Asp Leu Asn Thr Ser Ser Ser Tyr Val Gln Gly Lys Ile Ala
        195                 200                 205

Ala Tyr Leu Asn Asp Leu Val Ser Leu Gly Val Asp Gly Leu Arg Ile
    210                 215                 220
```

```
Asp Ala Val Lys His Ile Ala Ala Ser Asp Met Gln Gly Ile Leu Ser
225                 230                 235                 240

Lys Val Asn Asp Arg Ala Arg Leu Tyr Ile Val Gln Glu Val Ile Arg
            245                 250                 255

Ala Asn Glu Pro Ile Gln Pro Glu Glu Tyr Thr Ser Asn Gly Asp Ile
        260                 265                 270

His Glu Phe Ala Phe Ala Arg Lys Leu Lys Glu Ala Phe Asn Gly Gly
    275                 280                 285

Thr Ile Asn Trp Leu Thr Thr Gly Asn Gly Ile Gly Pro Thr Trp Ala
290                 295                 300

Gly Phe Leu Pro Asn Ala Asn Ala Ala Val Phe Val Asp Asn His Asp
305                 310                 315                 320

Thr Glu Arg Asn Gly Glu Thr Leu Thr Tyr Lys Asp Gly Ala Asn Tyr
            325                 330                 335

Asp Leu Ala Gln Ile Phe Thr Leu Ala Trp Asn Tyr Gly Ser Pro Ser
        340                 345                 350

Ile His Ser Gly Tyr Ser Phe Ser Asn Asn Asp Ala Gly Pro Ala Leu
    355                 360                 365

Ala Gly Asn Gly Glu Val Ile Asp Pro Val Cys Gly Gln Asn Gly Trp
370                 375                 380

Thr Cys Lys His Ala Gln Thr Gly Ile Glu Asn Met Val Gly Phe Arg
385                 390                 395                 400

Thr Gln Thr Tyr Gly Thr Ala Val Val Asn Lys Trp Asp Asn Gly Ser
            405                 410                 415

Ser Ala Ile Ala Phe Gly Arg Gly Asp Lys Gly Tyr Val Ala Ile Asn
        420                 425                 430

Arg Gly Ser Ala Leu Thr Arg Thr Phe Gln Thr Ser Leu Pro Ala Gly
    435                 440                 445

Asn Tyr Cys Asn Val Ile Val Gly Leu Pro Asn Ser Thr Gly Cys Ser
    450                 455                 460

Ala Gly Gly Val Val Thr Val Asp Ala Ala Gly Thr Phe Thr Ala Thr
465                 470                 475                 480

Val Asp Gln Asn Ser Ala Phe Ala Leu His Val Gly Ala Lys Ala Gly
            485                 490                 495

Thr Gln Gln Pro Gly Pro Gly Ala Gly Asp Met Lys Val Tyr Tyr Ser
        500                 505                 510

Thr Ser Lys Gly Trp Ser Asp Tyr Lys Ile His Tyr Arg Val Gly Thr
    515                 520                 525

Gly Ala Trp Thr Thr Ala Pro Gly Ala Gly Met Thr Ala Ala Cys Ala
530                 535                 540

Gly Trp Val Ser Tyr Thr Val Pro Ala Gly Ser Thr Gly Ala Thr Ala
545                 550                 555                 560

Ala Phe Asn Asn Gly Ser Gly Thr Trp Asp Asn Asn Thr Ser Asn
            565                 570                 575

Tyr Ala Leu Ser Gly Ala Val Ser Thr Val Asn Gly Val Val Gly
        580                 585                 590

His Thr Asp Pro Cys Thr Glu Ser Ala Pro Ala Asp Thr Ala
    595                 600                 605

Val Val Phe Tyr Ser Thr Asn Lys Gly Trp Ser Ala Tyr Asn Ile His
    610                 615                 620

Tyr Arg Val Gly Thr Gly Ala Trp Thr Thr Ala Pro Gly Ser Ala Met
625                 630                 635                 640

Thr Ala Ala Cys Thr Gly Trp Met Thr Ala Ser Ile Pro Leu Gly Gly
            645                 650                 655
```

```
Ala Ser Gly Ile Thr Ala Ala Phe Asn Asn Gly Ala Gly Thr Trp Asp
            660                 665                 670

Asn Asn Ala Gly Ala Asp Tyr Ser Val Gly Ser Gly Tyr Arg Gln Val
            675                 680                 685

Lys Asp Gly Val Val Ser Thr Gly Asn Pro Cys Ala
            690                 695                 700

<210> SEQ ID NO 4
<211> LENGTH: 683
<212> TYPE: PRT
<213> ORGANISM: Artificial
<220> FEATURE:
<223> OTHER INFORMATION: synthetic fusion protein

<400> SEQUENCE: 4

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala Ala Ala Pro
            20                  25                  30

Gly Pro Lys Asp Ala Thr Ala Val Met Phe Ser Trp Thr Trp Asn Ala
            35                  40                  45

Ile Ala Arg Glu Cys Thr Glu Asn Leu Gly Pro Ala Gly Tyr Gly Tyr
50              55                  60

Val Gln Thr Ser Pro Pro Gln Glu His Ile Gln Gly Ala Ala Trp Trp
65              70                  75                  80

Thr His Tyr Gln Pro Val Ser Tyr Lys Ile Glu Ser Arg Phe Gly Thr
            85                  90                  95

Arg Ala Glu Phe Lys Ala Met Val Asp Thr Cys His Ala Ala Gly Val
            100                 105                 110

Lys Val Ile Ala Asp Ala Val Ile Asn His Met Thr Gly Gln Ser Ala
            115                 120                 125

Gly Gly Thr Gly Trp Ala Gly Ser Thr Phe Gln His Tyr Asp Tyr Pro
            130                 135                 140

Gly Ile Tyr Gln Ser Gln Asp Phe His Ser Cys Arg Arg Asn Ile Ala
145             150                 155                 160

Asn Tyr Gln Asp Arg Trp Glu Val Gln Glu Cys Asn Leu Val Asn Leu
            165                 170                 175

Ala Asp Leu Asn Thr Ser Ser Tyr Val Gln Gly Lys Ile Ala Ala
            180                 185                 190

Tyr Leu Asn Asp Leu Val Ser Leu Gly Val Asp Gly Leu Arg Ile Asp
            195                 200                 205

Ala Val Lys His Ile Ala Ala Ser Asp Met Gln Gly Ile Leu Ser Lys
            210                 215                 220

Val Asn Asp Arg Ala Arg Leu Tyr Ile Val Gln Glu Val Ile Arg Ala
225             230                 235                 240

Asn Glu Pro Ile Gln Pro Glu Tyr Thr Ser Asn Gly Asp Ile His
            245                 250                 255

Glu Phe Ala Phe Ala Arg Lys Leu Lys Glu Ala Phe Asn Gly Gly Thr
            260                 265                 270

Ile Asn Trp Leu Thr Thr Gly Asn Gly Ile Gly Pro Thr Trp Ala Gly
            275                 280                 285

Phe Leu Pro Asn Ala Asn Ala Ala Val Phe Val Asp Asn His Asp Thr
            290                 295                 300

Glu Arg Asn Gly Glu Thr Leu Thr Tyr Lys Asp Gly Ala Asn Tyr Asp
305             310                 315                 320
```

```
Leu Ala Gln Ile Phe Thr Leu Ala Trp Asn Tyr Gly Ser Pro Ser Ile
            325                 330                 335

His Ser Gly Tyr Ser Phe Ser Asn Asn Asp Ala Gly Pro Ala Leu Ala
        340                 345                 350

Gly Asn Gly Glu Val Ile Asp Pro Val Cys Gly Gln Asn Gly Trp Thr
    355                 360                 365

Cys Lys His Ala Gln Thr Gly Ile Glu Asn Met Val Gly Phe Arg Thr
370                 375                 380

Gln Thr Tyr Gly Thr Ala Val Val Asn Lys Trp Asp Asn Gly Ser Ser
385                 390                 395                 400

Ala Ile Ala Phe Gly Arg Gly Asp Lys Gly Tyr Val Ala Ile Asn Arg
            405                 410                 415

Gly Ser Ala Leu Thr Arg Thr Phe Gln Thr Ser Leu Pro Ala Gly Asn
        420                 425                 430

Tyr Cys Asn Val Ile Val Gly Leu Pro Asn Ser Thr Gly Cys Ser Ala
    435                 440                 445

Gly Gly Val Val Thr Val Asp Ala Ala Gly Thr Phe Thr Ala Thr Val
    450                 455                 460

Asp Gln Asn Ser Ala Phe Ala Leu His Val Gly Ala Lys Ala Gly Thr
465                 470                 475                 480

Gln Gln Pro Gly Pro Gly Ala Gly Asp Met Lys Val Tyr Tyr Ser Thr
            485                 490                 495

Ser Lys Gly Trp Ser Asp Tyr Lys Ile His Tyr Arg Val Gly Thr Gly
        500                 505                 510

Ala Trp Thr Thr Ala Pro Gly Ala Gly Met Thr Ala Ala Cys Ala Gly
    515                 520                 525

Trp Val Ser Tyr Thr Val Pro Ala Gly Ser Thr Gly Ala Thr Ala Ala
530                 535                 540

Phe Asn Asn Gly Ser Gly Thr Trp Asp Asn Asn Thr Ser Asn Tyr
545                 550                 555                 560

Ala Leu Ser Gly Ala Val Ser Thr Val Asn Gly Val Val Gly His
            565                 570                 575

Thr Asp Pro Cys Thr Glu Ser Ala Pro Ala Pro Ala Thr Ala Val
        580                 585                 590

Val Phe Tyr Ser Thr Asn Lys Gly Trp Ser Ala Tyr Asn Ile His Tyr
    595                 600                 605

Arg Val Gly Thr Gly Ala Trp Thr Thr Ala Pro Gly Ser Ala Met Thr
    610                 615                 620

Ala Ala Cys Thr Gly Trp Met Thr Ala Ser Ile Pro Leu Gly Gly Ala
625                 630                 635                 640

Ser Gly Ile Thr Ala Ala Phe Asn Asn Gly Ala Gly Thr Trp Asp Asn
            645                 650                 655

Asn Ala Gly Ala Asp Tyr Ser Val Gly Ser Gly Tyr Arg Gln Val Lys
        660                 665                 670

Asp Gly Val Val Ser Thr Gly Asn Pro Cys Ala
    675                 680

<210> SEQ ID NO 5
<211> LENGTH: 10
<212> TYPE: PRT
<213> ORGANISM: Bacillus sp.

<400> SEQUENCE: 5

Ala Ala Pro Gly Pro Lys Asp Ala Thr Ala
1               5                   10
```

DETERGENT COMPOSITIONS AND METHODS OF USE FOR AN ALPHA-AMYLASE POLYPEPTIDE OF BACILLUS SPECIES 195

PRIORITY

The present application is a continuation application of U.S. application Ser. No. 12/519,879 filed on Sep. 16, 2009, now issued as U.S. Pat. No. 8,097,444, which claims priority under 35 USC §371 to International Application No. PCT/US2007/024959, filed Dec. 6, 2007, which claims the benefit of U.S. Provisional Patent Application Ser. No. 60/876,241, filed Dec. 21, 2006 and U.S. Provisional Patent Application Ser. No. 60/880,236, filed on Jan. 12, 2007, each of which are hereby incorporated by reference in their entirety.

SEQUENCE LISTING The sequence listing submitted via EFS, in compliance with 37 C.F.R. §1.52(e), is incorporated herein by reference. The sequence listing text file submitted via EFS contains the file "30948-PCT-seqlist", created on Nov. 28, 2011, which is 16,155,972 bytes in size.

FIELD OF THE INVENTION

Disclosed herein are compositions and methods of using α-amylase enzymes obtained from *Bacillus* sp. 195.

BACKGROUND

Starch consists of a mixture of amylose (15-30% w/w) and amylopectin (70-85% w/w). Amylose consists of linear chains of α-1,4-linked glucose units having a molecular weight (MW) from about 60,000 to about 800,000. Amylopectin is a branched polymer containing α-1,6 branch points every 24-30 glucose units; its MW may be as high as 100 million.

Sugars from starch, in the form of concentrated dextrose syrups, are currently produced by an enzyme catalyzed process involving: (1) liquefaction (or viscosity reduction) of solid starch with an α-amylase into dextrins having an average degree of polymerization of about 7-10, and (2) saccharification of the resulting liquefied starch (i.e. starch hydrolysate) with amyloglucosidase (also called glucoamylase or GA). The resulting syrup has a high glucose content. Much of the glucose syrup that is commercially produced is subsequently enzymatically isomerized to a dextrose/fructose mixture known as isosyrup.

α-amylases (EC 3.2.1.1) hydrolyze starch, glycogen, and related polysaccharides by cleaving internal α-1,4-glucosidic bonds at random. This enzyme has a number of important commercial applications in, for example the sugar, brewing, alcohol and textile industries. α-amylases are isolated from a wide variety of bacterial, fungal, plant and animal sources. Industrially, many important α-amylases are those isolated from *Bacilli*.

For a number of years, α-amylase enzymes have been used for a variety of different purposes, including starch liquefaction, textile desizing, starch modification in the paper and pulp industry, and for brewing. These enzymes also can be used to remove starchy stains during dishwashing and laundry washing.

One *Bacillus* α-amylase that has been sequenced is that from *Bacillus* sp. no. 195 (BAA). It consists of two domains: a catalytic domain similar to animal α-amylases and a domain that contains two starch binding motifs. See J. Sumitani et al., "New type of starch-binding domain: the direct repeat motif in the C-terminal region of *Bacillus* sp. no. 195 α-amylase contributes to starch binding and raw starch degrading," *Biochem. J.* 350: 477-484 (2000). In Sumitani et al., (2000), three active forms of the gene products were found in the culture supernatant of *Streptomyces lividans*, in which the *Bacillus* sp. no. 195 gene product was expressed heterologously. The three products were a 69 kDa form, a 60 kDa form, and a 50 kDa form. The 69 kDa form appears to be the full size mature protein with the molecular weight equivalent to that calculated based on the nucleotide sequence of the full length gene. The 60 kDa form appeared to be the same as that of the natural enzyme of *Bacillus* sp. no. 195 and was presumed to be generated by proteolytic processing between the two starch binding motifs located in the C-terminus. This form had lower activity for raw starch binding and degradation as compared to the 69 kDa form. The 50 kD form cannot bind or degrade insoluble starches.

Amylases have been used in textile processing, laundry and cleaning compositions, desizing compositions, and in baking, starch liquefaction and processing. Thus, there is a continuing need to identify α-amylases that are easier to produce at reduced costs, improve cost margins, deliver plant capacity savings, and higher activity products.

SUMMARY

Accordingly, an aspect is directed to an α-amylase from *Bacillus* sp. 195 that can be produced in an increased amount and at lower cost, as well addressing other needs in the industry. These variants can be used in a variety of compositions and processes that use α-amylases.

An object is to provide a nucleic acid, in one alternative an optimized nucleic acid depicted in FIG. 2 (SEQ ID NO: 2). Another aspect provides for the α-amylase gene being operably linked to a nucleic acid sequence encoding a signal peptide of *Bacillus licheniformis* α-amylase or a truncated polypeptide thereof.

It is yet another aspect that provides for a nucleic acid which encodes a truncated form of the polypeptide depicted in FIG. 4, wherein the truncation can occur at any residue after amino acid 491 (e.g., amino acid 492, 494, 504, 509, after any starch binding domain, and the like).

A further aspect provides for the full-length polypeptide of FIG. 4 or any carboxy-terminal truncated product after residue 491.

A further embodiment provides for a vector operably linked to the nucleic acid encoding the aforementioned polypeptides.

Yet a further aspect contemplates an isolated host cell with any of the above nucleic acids or vectors comprising said nucleic acids. The isolated host cell can be a prokaryote or eukaryote.

The isolated host cell can be a bacterium (e.g., *B. subtilis, B. licheniformis, B. lentus, B. brevis, B. stearothermophilus, B. alkalophilus, B. amyloliquefaciens, B. coagulans, B. circulans, B. lautus, B. thuringiensis, Streptomyces lividans, S. murinus,* or *Escherichia coli*).

Another aspect contemplates a detergent additive comprising a polypeptide described herein, wherein the detergent additive is optionally in the form of a non-dusting granulate, microgranulate, stabilized liquid, gel, or protected enzyme. The polypeptide in the detergent additive can be a truncated polypeptide as described above. The detergent additive can contain about 0.02 mg to about 200 mg of polypeptide per gram of the detergent additive. The detergent additive can further comprise an enzyme selected from the group consisting of a protease, a lipase, a peroxidase, an oxidase, an amylolytic enzyme, a cellulase, a polyesterase, and any combination thereof.

Another aspect contemplates a detergent composition comprising any of the described detergent additives. A detergent composition can optionally comprise one or more of: a surfactant, a bleaching system or bleach, a detergent builder, a polymer, a stabilizing agent, a fabric conditioner, a foam booster, a suds suppressor, an anti-corrosion agent, a dye, a perfume, a soil suspending agent, a tarnish inhibitor, an optical brightener, or a bactericide. A detergent composition can comprise or further comprise an additional enzyme, wherein the enzyme is a protease, a lipase, a peroxidase, an oxidase, an amylolytic enzyme, a cellulase, a polyesterase, or any combination thereof.

Another aspect contemplates a manual or automatic dishwashing detergent composition comprising a polypeptide described herein.

Yet a further aspect contemplates a method of washing dishes comprising applying a manual or automatic dishwashing detergent described herein to a dish or dishes in need thereof. The method of washing the dishes contemplates adding the dishwashing detergent in an amount such that the wash liquor contains a polypeptide described herein in the amount of about 0.01 ppm to about 4 ppm.

Another aspect contemplates a laundry detergent composition comprising a detergent additive described herein. Yet a further aspect contemplates a method of cleaning a textile comprising washing a soiled textile in solution with a detergent composition described herein. The method further contemplates having the polypeptide described herein in an amount in the solution of about 0.01 to about 2 ppm in the solution.

BRIEF DESCRIPTION OF THE DRAWINGS

FIGS. 1A-B. Nucleotide coding sequence of Bacillus sp. 195 α-amylase (Accession No. AB006823). The nucleotide sequence encoding the amy195 signal peptide is underlined. The STOP-codon is indicated in bold. SEQ ID NO: 1.

FIG. 2. Nucleotide coding sequence of Bacillus sp. 195 α-amylase after codon optimization. The nucleotide sequence encoding the mature amy 195 protein is preceded by a nucleotide sequence encoding the signal peptide of the B. licheniformis α-amylase (LAT) (SEQ ID NO: 2). The nucleotide sequence encoding the LAT signal peptide is underlined. The stop-codon is indicated in bold. Amino acid codon optimization was performed by GeneArt® (GeneArt GmbH, Germany).

FIG. 3. Polypeptide sequence of Amy195 (SEQ ID NO: 3). The signal sequence is residues 1-46 (underlined). The mature Amyl 95 begins at residue 47. The codons encoding the bold, underlined residues were replaced with a stop codon to generate the genetically truncated forms. Thus, Y511, K521 and V526, using the numbering of FIG. 3, are the last amino acid residues of the genetically truncated forms.

FIG. 4. Amy195 amino acid sequence depicted as a heterologous fusion protein with the LAT signal sequence (SEQ ID NO: 4). The lower case letters in the carboxy terminus form starch binding domains belonging to family CBD-25. The lower case letters (residues 1-29) at the amino terminus represent the amylase signal sequence obtained from B. licheniformis. The capital letters depict the catalytic domain of the enzyme including subdomains A, B, and C, which are expected to span approximately residues 30 to 105 and 208 to 300 for subdomain A; approximately residues 106 to 207 for subdomain B; and approximately 301 to 492 for subdomain C. Val492 is the last amino acid residue of the proteolytically truncated form (using the numbering in FIG. 4. Note that subdomain A is discontinuous in the linear sequence of the polypeptide.

DETAILED DESCRIPTION

Figure 5:
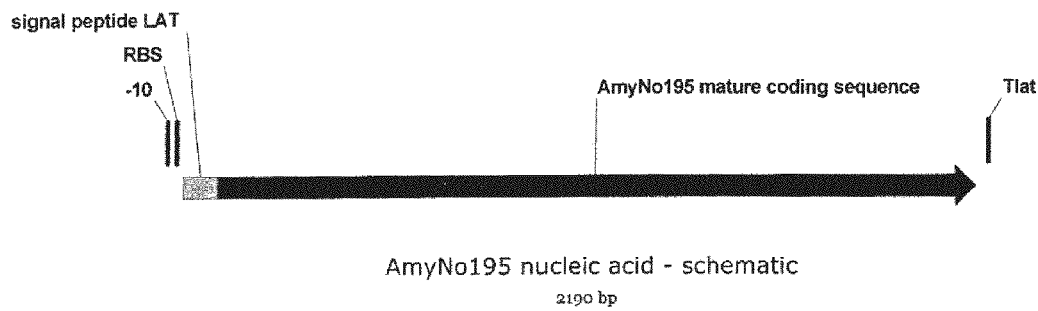
FIG. 5. Schematic of the linkage of the nucleic acid encoding the α-amylase of Bacillus sp. 195 to the nucleic acid encoding the LAT signal sequence and to the LAT terminator sequence in the pHPLT vector. The pHPLT plasmid is known in the art (see, e.g., U.S. Pat. Nos. 5,871,550, and 6,562,612, and US Pat. Publication 20060014265). The pHPLT vector was introduced into, and the amy195 gene expressed in, a nine protease deleted B. subtilis strain (see US20050202535A 1).

The application deals with compositions comprising Bacillus sp. no. 195 α-amylase and methods of use. Also disclosed are variations on how to produce α-amylase and heterologous forms by modifying the polypeptide sequence of the mature α-amylase.

Laundry and dish soils vary greatly in composition and therefore also in their ability to be removed. Relatively few amylases in the market place can be used for both laundry and dish applications. The α-amylase obtained from Bacillus sp. 195 does not show high identity with any of bacterial amylases in commercial use. Thus, one aspect is to use the wild-type protein as the backbone for identifying variants thereof with enhanced characteristics for dish and laundry by, e.g., reducing $Ca^{2+}$ dependence, improving LAS stability, improving pH ranges, improving temperature ranges, enhanced specific activity, and the like.

1. Definitions and Acronyms

In accordance with this detailed description, the following abbreviations and definitions apply. It must be noted that as used herein, the singular forms "a", "an", and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

Unless defined otherwise, all technical and scientific terms used herein have the same meaning as commonly understood by one of ordinary skill in the art. The following terms are provided below.

1.1 Acronyms

The following acronyms have the associated meanings unless defined otherwise in the context discussed within the specification.

AE alcohol ethoxylate
AEO alcohol ethoxylate
AEOS alcohol ethoxysulfate
AES alcohol ethoxysulfate
Amy195 α-amylase from Bacillus sp. no. 195
AOS α-olefinsulfonate
AS alkyl sulfate
CBD-25 carbohydrate binding domain protein family 25
cDNA complementary DNA
CMC carboxymethylcellulose
DNA deoxyribonucleic acid
DTMPA diethylenetriaminepentaacetic acid
EC enzyme commission
EDTA ethylenediaminetetraacetic acid
EMPA Eidgenössische Materialprüfungs- and Forschungs Anstalt (Swiss Federal Laboratories for Materials Testing and Research)
EO ethylene oxide (polymer fragment)
F&HC fabric & household care
GA glucoamylase
IPTG isopropyl β-D-thiogalactoside
kDa kilo Dalton
LAS linear alkylbenzenesulfonate
LAT pertaining to B. licheniformis amylase (e.g., B. licheniformis amylase signal sequence or terminator)
MW molecular weight
MWU modified Wohlgemuth unit; $1.6 \times 10^{-5}$ mg/MWU=unit of activity
NOBS nonanoyloxybenzenesulfonate
NTA nitriloacetic acid
OxAm Purastar HPAM 5000L (Genencor International, Inc.)
PEG polyethyleneglycol
pI isoelectric point
PVA polyvinyl alcohol)
PVP poly(vinylpyrrolidone)
RNA ribonucleic acid
SAS alkanesulfonate
SDS PAGE sodium dodecyl sulfate polyacrylamide gel electrophoresis
sp. species
TAED tetraacetylethylenediamine
w/v weight/volume
w/w weight/weight 1.2 Definitions The terms "amylase" or "amylolytic enzyme" are meant to include any amylase such as glucoamylases, α-amylase, β-amylases, the wild-type α-amylase of Bacillus sp., such as B. licheniformis and B. subtilis. "Amylase" shall mean an enzyme that is, among other things, capable of catalyzing the degradation of starch. Amylases are hydrolases that cleave the α-D-(1→4) O-glycosidic linkages in starch. Generally, α-amylases (EC 3.2.1.1; α-D-(1→4)-glucan glucanohydrolase) are defined as endo-acting enzymes cleaving α-D-(1→4) O-glycosidic linkages within the starch molecule in a random fashion. In contrast, the exo-acting amylolytic enzymes, such as β-amylases (EC 3.2.1.2; α-D-(1→4)-glucan maltohydrolase) and some product-specific amylases like maltogenic α-amylase (EC 3.2.1.133) cleave the starch molecule from the non-reducing end of the substrate. β-Amylases, α-glucosidases (EC 3.2.1.20; α-D-glucoside glucohydrolase), glucoamylase (EC 3.2.1.3; α-D-(1→4)-glucan glucohydrolase), and product-specific amylases can produce malto-oligosaccharides of a specific length from starch.

By "amylase variant", "α-amylase variant", "α-amylase variant polypeptide", and "variant enzyme" are meant an α-amylase protein of Bacillus sp. no. 195 that has been modified for example by using a signal sequence of another α-amylase and has been sequence optimized. As used herein, "parent enzymes," "parent sequence", "parent polypeptide", "wild-type α-amylase protein", and "parent polypeptides" shall mean enzymes and polypeptides from which the α-amylase variant polypeptides are derived. The parent enzyme may be a wild-type enzyme or an α-amylase that had previously been recombinantly engineered. Thus, the α-amylase polypeptide can be a recombinantly engineered enzyme. The α-amylase variant can also be a fusion protein containing a heterologous α-amylase polypeptide. For example, the α-amylase protein can comprise the signal peptide of B. licheniformis α-amylase (LAT) linked to the mature protein of another Bacillus α-amylase. The term "variant" may be used interchangeably with the term "mutant". Variants shall include polypeptides as well as nucleic acids. Variants shall include insertions; these variants can further contain additional substitutions, insertions, transversions, truncations, and/or inversions, at one or more locations. Variants can include sequences that are complementary to sequences that are capable of hybridizing to the nucleotide sequences presented herein. For example, a variant sequence is complementary to sequences capable of hybridizing under stringent conditions (e.g., 50° C. and 0.2×SSC {1×SSC=0.15 M NaCl, 0.015 M $Na_3$ citrate, pH 7.0}) to the nucleotide sequences presented herein. The term variant can further encompass sequences that are complementary to sequences that are capable of hybridizing under high stringent conditions (e.g., 65° C. and 0.1×SSC {1×SSC=0.15 M NaCl, 0.015 M $Na_3$ citrate, pH 7.0}) to the nucleotide sequences presented herein.

By "α-amylase of Bacillus sp. 195," "Amy195 α-amylase", or "Amy195" are meant the nucleic acid (FIG. 1) encoding the protein of FIG. 3 or the synthetic nucleic acid sequence of FIG. 2, which also encodes the protein of FIG. 4. It can also include any truncated form (i.e., truncated after residue 492 naturally, recombinantly or synthetically, an enzyme form without the signal sequence, or a form with a heterologous signal sequence and truncated at the carboxy terminus). In addition, the terms can include any derivative sequence of FIG. 3 and underlying DNA sequence containing amino acid substitutions, deletions, insertions, or amino acid extensions at the N- or C-termini that are not found in nature.

By "isolated" is meant that the sequence is at least substantially free from at least one other component that the sequence is naturally associated and found in nature.

By "purified" is meant that the material is in a relatively pure state, e.g., at least about 90% pure, or at least about 95% pure, or at least about 98% pure.

By "thermostable" is meant the ability of the enzyme to retain activity after exposure to elevated temperatures. The thermostability of an enzyme, such as an α-amylase, is measured by its half-life. The half-life ($t_{1/2}$) is the time in minutes, hours, or days, during which half the enzyme activity is lost under defined conditions. The half-life value is calculated by measuring the residual α-amylase activity.

By "pH range" is meant the ability of the enzyme to exhibit catalytic activity from acidic to basic conditions spanning 5 or more pH units.

As used herein, "pH stable" relates to the ability of the enzyme to retain activity over a wide range of pHs.

As used herein, "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

As used herein, "nucleotide sequence" or "nucleic acid sequence" refers to an oligonucleotide sequence or polynucleotide sequence, and variant, homologues, fragments and derivatives thereof (such as portions thereof). The nucleotide sequence may be of genomic or synthetic or recombinant origin, and may be double-stranded or single-stranded whether representing the sense or anti-sense strand. As used herein, the term nucleotide sequence includes genomic DNA, cDNA, synthetic DNA, and RNA.

"Homologue" shall mean an entity having a certain degree of identity with the subject amino acid sequences and the subject nucleotide sequences. A homologous sequence is taken to include an amino acid sequence at least 75%, 80%, 85% or 90% identical, or at least 95%, 96%, 97%, 98% or 99% identical to the subject sequence. Typically, homologues will comprise the same active sites as the subject amino acid sequence.

As used herein, "hybridization" shall include the process by which a strand of nucleic acid joins with a complementary strand through base pairing, as well as the process of amplification as carried out in polymerase chain reaction (PCR) technologies. The α-amylase variant nucleic acid may exist as single- or double-stranded DNA or RNA, an RNA/DNA heteroduplex or an RNA/DNA copolymer.

As used herein, "copolymer" refers to a single nucleic acid strand that comprises both ribonucleotides and deoxyribonucleotides. The α-amylase nucleic acid may even be codon optimized to further increase expression.

As used herein, "synthetic" shall refer to that which is produced by in vitro chemical or enzymatic synthesis. It includes, but is not limited to, α-amylase variant nucleic acids made with optimal codon usage for host organisms, such as but not limited to Pichia, Streptomyces, Trichoderma reesei, and Hansenula.

As used herein, "transformed cell" shall include cells that have been genetically altered by use of recombinant DNA techniques. Transformation typically occurs by insertion of one or more nucleotide sequences into a cell. The inserted nucleotide sequence may be a heterologous nucleotide sequence (i.e. is a sequence that is not natural to the cell that is to be transformed, such as a sequence encoding a fusion protein).

As used herein, "operably linked" shall mean that the components described are in a relationship permitting them to function in their intended manner. A regulatory sequence operably linked to a coding sequence is ligated in such a way that expression of the coding sequence is achieved under condition compatible with the control sequences.

As used herein, "biologically active" shall refer to a sequence having a similar structural function (but not necessarily to the same degree), and/or similar regulatory function (but not necessarily to the same degree) and/or similar biochemical function (but not necessarily to the same degree) of the naturally occurring sequence.

2. Nucleic Acids and Polypeptides Encoded Thereby

The nucleic acid sequence of Bacillus sp. no. 195 can be operably linked to various promoters and regulators in a vector and expressed in various host cells. The 2,103 residue nucleic acid sequence is disclosed at GenBank Accession No. AB006823 (see FIGS. 1A-B). The polypeptide sequence encoded by the 2,103 residue nucleic acid sequence is disclosed at GenBank Accession No. BAA22082.1 and is 700 amino acids in length (FIG. 3). The first 46 amino acids form the signal peptide. Cleavage occurs after residue 46 (Ala46).

When expressed in B. subtilis, there are three proteolytically processed forms of the protein seen by gel. These forms all have the same amino terminus but differ at their carboxy termini. The 49.5 kDa form terminates with residue Val492 (sequence in FIG. 4), i.e., proteolytic cleavage occurs after residue 492. The two longer forms, 69 kDa and 60 kDa, respectively contain one and two starch binding domains as discussed in Sumitani et al., (2000). Genetically C-terminally truncated forms were created with the products having C-terminal residues of Tyr494, Lys504, and Val509. These recombinantly produced truncation products all expressed at high levels in a nine protease deleted B. subtilis strain (see US20050202535A1) under LAT promoter and signal sequence control as displayed in FIG. 8.

2.1 Fusion Proteins and Recombinant Proteins

One aspect contemplates fusion proteins, wherein the signal sequences of amylases from other microorganisms, such as yeast or other bacterium, are used attached to the mature protein of Bacillus sp. no. 195. Namely, the first 46 amino acids that form the signal sequence of FIG. 3 can be removed and exchanged with the signal sequence from another microorganism or a variant of a signal sequence from another microorganism. For example, the LAT sequence (underlined and lower case) can be substituted for the first 46 amino acids as shown in FIG. 4.

Other examples include but are not limited to B. subtilis amylase (amyE) signal sequence for expression in B. subtilis, the B. subtilis aprE promoter and signal sequences also for expression in B. subtilis. In addition, it is contemplated to test expression in Streptomyces sp. with the use of Streptomyces promoters and signal sequences from CelA.

3. Method of Producing and Purifying Proteins Methods of producing and purifying proteins that are secreted in to the culture medium from Bacillus are known in the art, as are suitable host cells for producing α-amylases. Exemplary methods for producing the α-amylases are disclosed below.

3.1 Materials and Methods for Producing α-Amylases

A DNA sequence encoding the Amy 195 α-amylase or variant thereof produced by methods described herein, or by any alternative methods known in the art, can be expressed, in enzyme form, using an expression vector which typically includes control sequences encoding a suitable promoter, operator, ribosome binding site, translation initiation signal, and, optionally, a repressor gene or various activator genes.

For example, the *Bacillus* sp. no. 195 can be grown at 30° C. as described in T. Kawaguchi et al., "Purification and some properties of a Haim-sensitive α-amylase from newly isolated *Bacillus* sp. No. 195," *Biose. Biotechnol. Biochem.* 56: 1792-1796 (1992). Alternatively, a gene encoding the α-amylase operably linked to a vector can be transfected in to another organism, such as *Streptomyces lividans* TK-24 and cultured under appropriate conditions as described in J. Sumitani et al., "New type of starch-binding domain: the direct repeat motif in the C-terminal region of *Bacillus* sp. no. 195 α-amylase contributes to starch binding and raw starch degrading," *Biochem. J.* 350: 477-484 (2000).

The recombinant expression vector carrying the DNA sequence encoding an Amyl 95 α-amylase or variant thereof may be any vector that may conveniently be subjected to recombinant DNA procedures, and the choice of vector will often depend on the host cell into which it is to be introduced. Thus, the vector may be an autonomously replicating vector, i.e., a vector that exists as an extrachromosomal entity, the replication of which is independent of chromosomal replication, e.g., a plasmid, a bacteriophage or an extrachromosomal element, mini-chromosome or an artificial chromosome. Alternatively, the vector may be one which, when introduced into an isolated host cell, is integrated into the host cell genome and replicated together with the chromosome(s) into which it has been integrated. The integrated gene may also be amplified to create multiple copies of the gene in the chromosome by use of an amplifiable construct driven by antibiotic selection or other selective pressure, such as an essential regulatory gene or by complementation through dose effect of an essential metabolic pathway gene.

In the vector, the DNA sequence should be operably linked to a suitable promoter sequence. The promoter may be any DNA sequence that shows transcriptional activity in the host cell of choice and may be derived from genes encoding proteins either homologous or heterologous to the host cell. Exemplary promoters for directing the transcription of the DNA sequence encoding an Amy195 α-amylase or variant thereof, especially in a bacterial host, are the promoter of the lac operon of *E. coli*, the *Streptomyces coelicolor* agarase gene dagA or celA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase, or *A. nidulans* acetamidase. When the gene encoding the α-amylase variant polypeptide is expressed in a bacterial species such as *E. coli*, a suitable promoter can be selected, for example, from a bacteriophage promoter including a T7 promoter and a phage lambda promoter. Examples of suitable promoters for the expression in a yeast species include but are not limited to the Gal 1 and Gal 10 promoters of *Saccharomyces cerevisiae* and the *Pichia pastoris* AOX1 or AOX2 promoters. For expression in *Trichoderma reesei*, the CBHII (cellobiohydrolase II) promoter may be used.

An expression vector may also comprise a suitable transcription terminator and, in eukaryotes, polyadenylation sequences operably linked to the DNA sequence encoding Amy195 α-amylase or variants thereof. Termination and polyadenylation sequences may suitably be derived from the same sources as the promoter.

The vector may further comprise a DNA sequence enabling the vector to replicate in the host cell. Examples of such sequences are the origins of replication of plasmids pUC19, pACYC177, pUB110, pE194, pAMB1, and pIJ702.

The vector may also comprise a selectable marker, e.g., a gene the product of which complements a defect in the isolated host cell, such as the dal genes from *B. subtilis* or *B. licheniformis*, or a gene that confers antibiotic resistance such as, e.g., ampicillin, kanamycin, chloramphenicol or tetracycline resistance. Furthermore, the vector may comprise *Aspergillus* selection markers such as amdS, argB, niaD and xxsC, a marker giving rise to hygromycin resistance, or the selection may be accomplished by co-transformation, such as known in the art. See e.g., International PCT Application WO 91/17243.

While intracellular expression or solid-state fermentation may be advantageous in some respects, e.g., when using certain bacteria or fungi as host cells, one aspect contemplates expression of the Amy195 α-amylase or variant thereof into the culture medium. In general, the α-amylase comprises a signal sequence at the amino terminus that permits secretion into the culture medium. If desirable, this signal peptide may be replaced by a different sequence, conveniently accomplished by substitution of the DNA sequences encoding the respective signal polypeptide. The signal sequences of α-amylases are typically characterized as having three domains, an N-terminal domain, an H-domain, and a C-terminal domain and typically range from 18 to 35 residues in length, but can be longer as exemplified with the Amy195 signal sequence.

The expression vector typically includes the components of a cloning vector, such as, for example, an element that permits autonomous replication of the vector in the selected host organism and one or more phenotypically detectable markers for selection purposes. The expression vector normally comprises control nucleotide sequences such as a promoter, operator, ribosome binding site, translation initiation signal and optionally, a repressor gene or one or more activator genes. Additionally, the expression vector may comprise a sequence coding for an amino acid sequence capable of targeting the α-amylase variant to a host cell organelle such as a peroxisome, or to a particular host cell compartment. Such a targeting sequence includes but is not limited to the sequence, SKL. For expression under the direction of control sequences, the nucleic acid sequence of the α-amylase variant is operably linked to the control sequences in proper manner with respect to expression. A portion of an exemplary vector is depicted in FIG. 5.

The procedures used to ligate the DNA construct encoding an α-amylase variant, the promoter, terminator and other elements, respectively, and to insert them into suitable vectors containing the information necessary for replication, are well known to persons skilled in the art (see e.g., Sambrook et al., MOLECULAR CLONING: A LABORATORY MANUAL, $2^{nd}$ ed., Cold Spring Harbor, 1989, and $3^{rd}$ ed., 2001).

An isolated cell, either comprising a DNA construct or an expression vector, is advantageously used as a host cell in the recombinant production of Amy195 α-amylase or variant thereof. The cell may be transformed with the DNA construct encoding the enzyme, conveniently by integrating the DNA construct (in one or more copies) in the host chromosome.

This integration is generally considered to be an advantage, as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

Examples of suitable bacterial host organisms are Gram positive bacterial species such as *Bacillaceae* including *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus lautus, Bacillus megaterium,* and *Bacillus thuringiensis; Streptomyces* species such as *Streptomyces murinus;* lactic acid bacterial species including *Lactococcus* spp. such as *Lactococcus lactis; Lactobacillus* spp. including *Lactobacillus reuteri; Leuconostoc* spp.; *Pediococcus* spp.; and *Streptococcus* spp. Alternatively, strains of a Gram negative bacterial species belonging to *Enterobacteriaceae* including *E. coli,* or to *Pseudomonadaceae* can be selected as the host organism.

A suitable yeast host organism can be selected from the biotechnologically relevant yeasts species such as but not limited to yeast species such as *Pichia* sp., *Hansenula* sp., or *Kluyveromyces, Yarrowinia, Schizosaccharomyces* species or a species of *Saccharomyces,* including *Saccharomyces cerevisiae* or a species belonging to *Schizosaccharomyces* such as, for example, *S. pombe* species. A strain of the methylotrophic yeast species, *Pichia pastoris,* can be used as the host organism. Alternatively, the host organism can be a *Hansenula* species. Suitable host organisms among filamentous fungi include species of *Aspergillus,* e.g., *Aspergillus niger, Aspergillus oryzae, Aspergillus tubigensis, Aspergillus awamori,* or *Aspergillus nidulans.* Alternatively, strains of a *Fusarium* species, e.g., *Fusarium oxysporum* or of a *Rhizomucor* species such as *Rhizomucor miehei* can be used as the host organism. Other suitable strains include *Thermomyces* and *Mucor* species. In addition, *Trichoderma reesei* can be used as a host. A suitable procedure for transformation of *Aspergillus* host cells includes, for example, that described in EP 238023.

In a yet further aspect, a method of producing α-amylase Amy195 or variant thereof is provided comprising cultivating a host cell as described above under conditions conducive to the production of the enzyme and recovering the enzyme from the cells and/or culture medium.

The medium used to cultivate the cells may be any conventional medium suitable for growing the host cell in question and obtaining expression of Amy195 α-amylase or variant thereof. Suitable media and media components are available from commercial suppliers or may be prepared according to published recipes (e.g., as described in catalogues of the American Type Culture Collection).

In one aspect, an enzyme secreted from the host cells is used in a whole broth preparation. In the methods of the present invention, the preparation of a spent whole fermentation broth of a recombinant microorganism can be achieved using any cultivation method known in the art resulting in the expression of an alpha-amylase. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the amylase to be expressed or isolated. The term "spent whole fermentation broth" is defined herein as unfractionated contents of fermentation material that includes culture medium, extracellular proteins (e.g., enzymes), and cellular biomass. It is understood that the term "spent whole fermentation broth" also encompasses cellular biomass that has been lysed or permeabilized using methods well known in the art.

An enzyme secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

An aspect contemplates the polynucleotide in a vector is operably linked to a control sequence that is capable of providing for the expression of the coding sequence by the host cell, i.e. the vector is an expression vector. The control sequences may be modified, for example by the addition of further transcriptional regulatory elements to make the level of transcription directed by the control sequences more responsive to transcriptional modulators. The control sequences may in particular comprise promoters.

Host cells may be cultured under suitable conditions that allow expression of the Amy195 α-amylase or variant thereof. Expression of the enzymes may be constitutive such that they are continually produced, or inducible, requiring a stimulus to initiate expression. In the case of inducible expression, protein production can be initiated when required by, for example, addition of an inducer substance to the culture medium, for example dexamethasone or IPTG or Sepharose. Polypeptides can also be produced recombinantly in an in vitro cell-free system, such as the TnT™ (Prornega) rabbit reticulocyte system.

An Amyl 95 α-amylase, or variant thereof, expressing host also can be cultured in the appropriate medium for the host, under aerobic conditions. Shaking or a combination of agitation and aeration can be provided, with production occurring at the appropriate temperature for that host, e.g., from about 25° C. to about 75° C. (e.g., 30° C. to 45° C.), depending on the needs of the host and production of the desired α-amylase variant. Culturing can occur from about 12 to about 100 hours or greater (and any hour value there between, e.g., from 24 to 72 hours). Typically, the culture broth is at a pH of about 5.5 to about 8.0, again depending on the culture conditions needed for the host relative to production of the α-amylase variant.

3.2 Materials and Methods for Protein Purification

Fermentation, separation, and concentration techniques are well known in the art and conventional methods can be used in order to prepare a concentrated Amyl 95 α-amylase or variant thereof containing solution.

After fermentation, a fermentation broth is obtained, the microbial cells and various suspended solids, including residual raw fermentation materials, are removed by conventional separation techniques in order to obtain an amylase solution. Filtration, centrifugation, microfiltration, rotary vacuum drum filtration, ultrafiltration, centrifugation followed by ultra-filtration, extraction, or chromatography, or the like, are generally used.

It is desirable to concentrate the Amy195 α-amylase or variant thereof containing solution in order to optimize recovery. Use of unconcentrated solutions requires increased incubation time in order to collect the purified enzyme precipitate.

The enzyme containing solution is concentrated using conventional concentration techniques until the desired enzyme level is obtained. Concentration of the enzyme containing solution may be achieved by any of the techniques discussed herein. Exemplary methods of purification include but are not limited to rotary vacuum filtration and/or ultrafiltration.

The enzyme solution is concentrated into a concentrated enzyme solution until the enzyme activity of said concentrated Amy195 α-amylase or variant thereof containing solution is at least about 4 g/L (e.g., at least about 4.8 g/L, or at least 5.6 g/L or even higher). These concentrations can be increased to as much as about 25 g/L under certain applications.

By "precipitation agent" for purposes of purification is meant a compound effective to precipitate the Amy195 α-amylase or variant thereof from the concentrated enzyme solution in solid form, whatever its nature may be, i.e. crystalline, amorphous or blend of both.

Precipitation can be performed using, for example, a metal halide precipitation agent. Metal halide precipitation agents include but are not limited to: alkali metal chlorides, alkali metal bromides and blends of two or more of these metal halides. Exemplary metal halides include sodium chloride, potassium chloride, sodium bromide, potassium bromide and blends of two or more of these metal halides. The metal halide precipitation agent, sodium chloride, can also be used as a preservative.

The metal halide precipitation agent is used in an amount effective to precipitate the Amy195 α-amylase or variant thereof. The selection of at least an effective amount and an optimum amount of metal halide effective to cause precipitation of the enzyme, as well as the conditions of the precipitation for maximum recovery including incubation time, pH, temperature and concentration of enzyme, will be readily apparent to one of ordinary skill in the art, after routine testing.

Generally, at least about 5% w/v (weight/volume) to about 25% w/v of metal halide is added to the concentrated enzyme solution, and usually at least 8% w/v. Generally, no more than about 25% w/v of metal halide is added to the concentrated enzyme solution and usually no more than about 20% w/v. The optimal concentration of the metal halide precipitation agent will depend, among others, on the nature of the specific Amy195 α-amylase variant and on its concentration in the concentrated enzyme solution.

Another alternative to effect precipitation of the enzyme is to use organic compounds. Exemplary organic compound precipitating agents include: 4-hydroxybenzoic acid, alkali metal salts of 4-hydroxybenzoic acid, alkyl esters of 4-hydroxybenzoic acid, and blends of two or more of these organic compounds. The addition of said organic compound precipitation agents can take place prior to, simultaneously with or subsequent to the addition of the metal halide precipitation agent, and the addition of both precipitation agents, organic compound and metal halide, may be carried out sequentially or simultaneously.

For further descriptions, see, e.g., U.S. Pat. No. 5,281,526. Generally, the organic precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitation agents can be, for example, linear or branched alkyl esters of 4-hydroxybenzoic acid, wherein the alkyl group contains from 1 to 10 carbon atoms, and blends of two or more of these organic compounds. Exemplary organic compounds are linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl esters of 4-hydroxybenzoic acid, butyl ester of 4-hydroxybenzoic acid, ethyl ester of 4-hydroxybenzoic acid and blends of two or more of these organic compounds can also be used. Additional organic compounds also include but are not limited to 4-hydroxybenzoic acid methyl ester (named methyl PARABEN), 4-hydroxybenzoic acid propyl ester (named propyl PARABEN), which also are both amylase preservative agents.

Addition of the organic compound precipitation agent provides the advantage of high flexibility of the precipitation conditions with respect to pH, temperature, Amy195 α-amylase or variant thereof concentration, precipitation agent concentration, and time of incubation.

The organic compound precipitation agent is used in an amount effective to improve precipitation of the enzyme by means of the metal halide precipitation agent. The selection of at least an effective amount and an optimum amount of organic compound precipitation agent, as well as the conditions of the precipitation for maximum recovery including incubation time, pH, temperature and concentration of enzyme, will be readily apparent to one of ordinary skill in the art, in light of the present disclosure, after routine testing.

Generally, at least about 0.01% w/v of organic compound precipitation agent is added to the concentrated enzyme variant solution and usually at least about 0.02% w/v. Generally, no more than about 0.3% w/v of organic compound precipitation agent is added to the concentrated enzyme variant solution and usually no more than about 0.2% w/v.

The concentrated enzyme solution, containing the metal halide precipitation agent, and the organic compound precipitation agent, can be adjusted to a pH, which will, of necessity, depend on the enzyme to be purified. Generally, the pH is adjusted at a level near the isoelectric point of the amylase. The pH can be adjusted at a pH in a range from about 2.5 pH units below the isoelectric point (pI) up to about 2.5 pH units above the isoelectric point.

The incubation time necessary to obtain a purified enzyme precipitate depends on the nature of the specific enzyme, the concentration of enzyme, and the specific precipitation agent(s) and its (their) concentration. Generally, the time effective to precipitate the enzyme is between about 1 to about 30 hours; usually it does not exceed about 25 hours. In the presence of the organic compound precipitation agent, the time of incubation can still be reduced to less about 10 hours and in most cases even about 6 hours.

Generally, the temperature during incubation is between about 4° C. and about 50° C. Usually, the method is carried out at a temperature between about 10° C. and about 45° C. (e.g., between about 20° C. and about 40° C.). The optimal temperature for inducing precipitation varies according to the solution conditions and the enzyme or precipitation agent(s) used.

The overall recovery of purified enzyme precipitate, and the efficiency with which the process is conducted, is improved by agitating the solution comprising the enzyme, the added metal halide and the added organic compound. The agitation step is done both during addition of the metal halide and the organic compound, and during the subsequent incubation period. Suitable agitation methods include mechanical stirring or shaking, vigorous aeration, or any similar technique.

After the incubation period, the purified enzyme is then separated from the dissociated pigment and other impurities and collected by conventional separation techniques, such as filtration, centrifugation, microfiltration, rotary vacuum filtration, ultrafiltration, press filtration, cross membrane microfiltration, cross flow membrane microfiltration, or the like.

Further purification of the purified enzyme precipitate can be obtained by washing the precipitate with water. For example, the purified enzyme precipitate is washed with water containing the metal halide precipitation agent, or with water containing the metal halide and the organic compound precipitation agents.

During fermentation, the Amy195 α-amylase or variant thereof accumulates in the culture broth. For the isolation and purification of the desired α-amylase variant, the culture broth is centrifuged or filtered to eliminate cells, and the resulting cell-free liquid is used for enzyme purification. In one embodiment, the cell-free broth is subjected to salting out using ammonium sulfate at about 70% saturation; the 70% saturation-precipitation fraction is then dissolved in a buffer and applied to a column such as a Sephadex G-100 column, and eluted to recover the enzyme-active fraction. For further purification, a conventional procedure such as ion exchange chromatography may be used.

Purified enzymes are useful for laundry and cleaning applications. For example, they can be used in laundry detergents and spot removers. They can be made into a final product that is either liquid (solution, slurry) or solid (granular, powder).

A more specific example of purification, is described in J. Sumitani et al., "New type of starch-binding domain: the direct repeat motif in the C-terminal region of $Bacillus$ sp. no. 195 α-amylase contributes to starch binding and raw starch degrading," $Biochem.\ J.$ 350: 477-484 (2000) and is briefly summarized here. The enzyme obtained from 4 liters of a $Streptomyces\ lividans$ TK24 culture supernatant was treated with $(NH_4)_2SO_4$ at 80% saturation. The precipitate was recovered by centrifugation at 10,000×g (20 minutes and 4° C.) and re-dissolved in 20 mM Tris/HCl buffer (pH 7.0) containing 5 mM $CaCl_2$. The solubilized precipitate was then dialyzed against the same buffer. The dialyzed sample was then applied to a Sephacryl S-200 column, which had previously been equilibrated with 20 mM Tris/HCl buffer, (pH 7.0), 5 mM $CaCl_2$, and eluted at a linear flow rate of 7 cm/hr with the same buffer. Fractions from the column were collected and assessed for activity as judged by enzyme assay and SDS-PAGE. The protein was further purified as follows. A Toyopearl HW55 column (Tosoh Bioscience, Montgomeryville, Pa.; Cat. No. 19812) was equilibrated with 20 mM Tris/HCl buffer (pH 7.0) containing 5 mM $CaCl_2$ and 1.5 M $(NH_4)_2SO_4$. The enzyme was eluted with a linear gradient of 1.5 to 0 M $(NH_4)_2SO_4$ in 20 mM Tris/HCl buffer, pH 7.0 containing 5 mM $CaCl_2$. The active fractions were collected, and the enzyme precipitated with $(NH_4)_2SO_4$ at 80% saturation. The precipitate was recovered, re-dissolved, and dialyzed as described above. The dialyzed sample was then applied to a Mono Q HR5/5 column (Amersham Pharmacia; Cat. No. 17-5167-01) previously equilibrated with 20 mM Tris/HCl buffer (pH 7.0) containing 5 mM $CaCl_2$, at a flow rate of 60 mL/hour. The active fractions are collected and added to a 1.5 M $(NH_4)_2SO_4$ solution. The active enzyme fractions were re-chromatographed on a Toyopearl HW55 column, as before, to yield a homogeneous enzyme as determined by SDS-PAGE. See J. Sumitani et al., "New type of starch-binding domain: the direct repeat motif in the C-terminal region of $Bacillus$ sp. no. 195 α-amylase contributes to starch binding and raw starch degrading," $Biochem.\ J.$ 350: 477-484 (2000) for general discussion of the method and variations thereon.

For production scale recovery, the enzyme can be partially purified as generally described above by removing cells via flocculation with polymers. Alternatively, the enzyme can be purified by microfiltration followed by concentration by ultrafiltration using available membranes and equipment. However, for some applications, the enzyme does not need to be purified, and whole broth culture can be lysed and used without further treatment. The enzyme can then be processed, for example, into granules.

4. Cleaning Compositions

The Amyl 95 α-amylase and variant(s) thereof possess valuable properties allowing for a variety of industrial applications. These enzymes can be used as a component in washing, dishwashing and hard-surface cleaning detergent compositions. They can be formulated as part of a detergent additive, as part of a detergent composition, as part of an automatic or hand wash dishwashing composition, and the like. The Amy195 α-amylase and variant(s) thereof may be incorporated in concentrations conventionally employed in detergents. It is at present contemplated that, in the detergent compositions, the α-amylase may be added in amount corresponding to 0.00001-1 mg (calculated as pure enzyme protein) of α-amylase per liter of wash/diswash liquor. Exemplary formulations are provided herein.

4.1 Laundry Detergent Composition

Accordingly, an Amy195 α-amylase or variant thereof may typically be a component of a detergent composition, as the only enzyme or with other enzymes including other amylolytic enzymes. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB Patent No. 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in for example EP 238,216. Polyols have long been recognized as stabilizers of proteins, as well as improving protein solubility. See, e.g., J. K. Kaushik et al., "Why is trehalose an exceptional protein stabilizer?" $J.\ Biol.\ Chem.$ 278: 26458-65 (2003) and references cited therein; and Monica Conti et al., "Capillary isoelectric focusing: the problem of protein solubility," $J.\ Chromatography\ A$ 757: 237-245 (1997).

The detergent composition may be in any useful form, e.g., as powders, granules, pastes, or liquid. A liquid detergent may be aqueous, typically containing up to about 70% of water and 0% to about 30% of organic solvent. It may also be in the form of a compact gel type containing only about 30% water.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO 92/06154).

The detergent composition may additionally comprise one or more other enzymes, such as lipase, another amylolytic enzyme, cutinase, protease, cellulase, peroxidase, and/or laccase in any combination.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e. essentially free of detergent builder. The enzymes can be used in any composition compatible with the stability of the enzyme. Enzymes generally can be protected against deleterious components by known forms of encapsulation, for example, by granulation or sequestration in hydro gels. Enzymes, and specifically α-amylases, such as amy195 molecules, either with or without starch binding domains, can be used in a variety of compositions including laundry and dishwashing applications, surface cleaners, as well as in compositions for ethanol production from starch or biomass.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate, which may be combined with a peracid-forming bleach activator such as tetraacetylethylenediamine (TAED) or nonanoyloxybenzenesulfonate (NOBS). Alternatively, the bleaching system may comprise peroxyacids (e.g., the amide, imide, or sulfone type peroxyacids). The bleaching system can also be an enzymatic bleaching system, for example, perhydrolase, such as that described in International PCT Application WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative such as, e.g., an aromatic borate ester; and the composition may be formulated as described in, e.g., WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, tarnish inhibiters, optical brighteners, or perfumes.

The pH (measured in aqueous solution at use concentration) is usually neutral or alkaline, e.g., pH about 7.0 to about 11.0.

Particular forms of detergent compositions comprising the Amy195 α-amylase or variants thereof can be formulated to include:

1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5% to about 9%; sodium carbonate (e.g., $Na_2CO_3$) about 14% to about 20%; soluble silicate (e.g., $Na_2O$, $2SiO_2$) about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6H_5Na_3O_7/C_6H_8O_7$) about 0% to about 15%; sodium perborate (e.g., $NaBO_3H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

2) A detergent composition formulated as a granulate having a bulk density of at least 600 g/L comprising linear alkylbenzenesulfonate (calculated as acid) about 6% to about 11%; alcohol ethoxysulfate (e.g., $C_{12-18}$ alcohol, 1-2 EO) or alkyl sulfate (e.g., $C_{16-18}$) about 1% to about 3%; alcohol ethoxylate (e.g., $C_{14-15}$ alcohol, 1-2 EO) about 5% to about 9%; sodium carbonate (e.g., $Na_2CO_3$) about 15% to about 21%; soluble silicate (e.g., $Na_2O$, $2SiO_2$) about 1% to about 4%; zeolite (e.g., $NaAlSiO_4$) about 24% to about 34%; sodium sulfate (e.g., $Na_2SO_4$) about 4% to about 10%; sodium citrate/citric acid (e.g., $C_6H_5Na_3O_7/C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

3) A detergent composition formulated as a granulate having a bulk density of at least 600 g/L comprising linear alkylbenzenesulfonate (calculated as acid) about 5%© to about 9%; alcohol ethoxylate (e.g., $C_{12-15}$ alcohol, 7 EO) about 7% to about 14%; Soap as fatty acid (e.g., $C_{16-22}$ fatty acid) about 1 to about 3%; sodium carbonate (as $Na_2CO_3$) about 10% to about 17%; soluble silicate (e.g., $Na_2O$, $2SiO_2$) about 3% to about 9%; zeolite (as $NaAlSiO_4$) about 23% to about 33%; sodium sulfate (e.g., $Na_2SO_4$) 0% to about 4%; sodium perborate (e.g., $NaBO_3H_2O$) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

4) A detergent composition formulated as a granulate having a bulk density of at least 600 g/L comprising linear alkylbenzenesulfonate (calculated as acid) about 8% to about 12%; alcohol ethoxylate (e.g., $C_{12-15}$ alcohol, 7 EO) about 10% to about 25%; sodium carbonate (as $Na_2CO_3$) about 14% to about 22%; soluble silicate (e.g., $Na_2O$, $2SiO_2$) about 1% to about 5%; zeolite (e.g., $NaAlSiO_4$) about 25% to about 35%; sodium sulfate (e.g., $Na_2SO_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

5) An aqueous liquid detergent composition comprising linear alkylbenzenesulfonate (calculated as acid) about 15% to about 21%; alcohol ethoxylate (e.g., $C_{12-15}$ alcohol, 7 EO or $C_{12-15}$ alcohol, 5 EO) about 12% to about 18%; soap as fatty acid (e.g., oleic acid) about 3% to about 13%; alkenylsuccinic acid ($C_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., $B_4O_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener)0-5%.

6) An aqueous structured liquid detergent composition comprising linear alkylbenzenesulfonate (calculated as acid) about 15% to about 21%; alcohol ethoxylate (e.g., $C_{12-15}$ alcohol, 7 EO, or $C_{12-15}$ alcohol, 5 EO) 3-9%; soap as fatty acid (e.g., oleic acid) about 3% to about 10%; zeolite (as $NaAlSiO_4$) about 14% to about 22%; potassium citrate about 9% to about 18%; borate (e.g., $B_4O_7$) 0% to about 2%; carboxymethylcellulose (CMC) 0% to about 2%; polymers (e.g., PEG, PVP) 0% to about 3%; anchoring polymers such as, e.g., lauryl methacrylate/acrylic acid copolymer; molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., $Na_2CO_3$) about 5% to about 10%; Soluble silicate (e.g., $Na_2O, 2SiO_2$) about 1% to about 4%; zeolite (e.g., $NaAlSiO_4$) about 20% to about 40%; Sodium sulfate (e.g., $Na_2SO_4$) about 2% to about 8%; sodium perborate (e.g., $NaBO_3H_2O$) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., $Na_2CO_3$) about 4% to about 10%; soluble silicate ($Na_2O, 2SiO_2$) about 1% to about 4%; zeolite (e.g., $NaAlSiO_4$) about 30% to about 50%; sodium sulfate (e.g., $Na_2SO_4$) about 3% to about 11%; sodium citrate (e.g., $C_6H_5Na_3O_7$) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., $Na_2CO_3$) about 14% to about 22%; zeolite (e.g., $NaAlSiO_4$) about 18% to about 32%; sodium sulfate (e.g., $Na_2SO_4$) about 5% to about 20%; sodium citrate (e.g., $C_6H_5Na_3O_7$) about 3% to about 8%; sodium perborate (e.g., $NaBO_3H_2O$) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

10) An aqueous liquid detergent composition comprising linear alkylbenzenesulfonate (calculated as acid) about 15% to about 23%; alcohol ethoxysulfate (e.g., $C_{12-15}$ alcohol, 2-3 EO) about 8% to about 15%; alcohol ethoxylate $C_{12-15}$ alcohol, 7 EO, or $C_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., $B_4O_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

11) An aqueous liquid detergent composition comprising linear alkylbenzenesulfonate (calculated as acid) about 20% to about 32%; alcohol ethoxylate $C_{12-15}$ alcohol, 7 EO, or $C_{12-15}$ alcohol, 5 EO) 6-12%; aminoethanol about 2% to about 6%; citric acid about 8% to about 14%; borate (e.g., $B_4O_7$) about 1% to about 3%; polymer (e.g., maleic/acrylic acid copolymer, anchoring polymer such as, e.g., lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., $Na_2CO_3$) about 8% to about 25%; soluble silicates (e.g., $Na_2O, 2SiO_2$) about 5% to about 15%; sodium sulfate (e.g., $Na_2SO_4$) 0% to about 5%; zeolite ($NaAlSiO_4$) about 15% to about 28%; sodium perborate (e.g., $NaBO_3 4H_2O$) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

13) Detergent compositions as described in compositions 1)-12) supra, wherein all or part of the linear alkylbenzenesulfonate is replaced by ($C_{12}$-$C_{18}$) alkyl sulfate.

14) A detergent composition formulated as a granulate having a bulk density of at least 600 g/L comprising ($C_{12}$-$C_{18}$) alkyl sulfate about 9% to about 15%; alcohol ethoxylate about 3% to about 6%; polyhydroxy alkyl fatty acid amide about 1% to about 5%; zeolite (e.g., $NaAlSiO_4$) about 10% to about 20%; layered disilicate (e.g., SK56 from Hoechst) about 10% to about 20%; sodium carbonate (e.g., $Na_2CO_3$) about 3% to about 12%; soluble silicate (e.g., $Na_2O, 2SiO_2$) 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

15) A detergent composition formulated as a granulate having a bulk density of at least 600 g/L comprising ($C_{12}$-$C_{18}$) alkyl sulfate about 4% to about 8%; alcohol ethoxylate about 11% to about 15%; soap about 1% to about 4%; zeolite MAP or zeolite A about 35% to about 45%; sodium carbonate (as $Na_2CO_3$) about 2% to about 8%; soluble silicate (e.g., $Na_2O, 2SiO_2$) 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

16) Detergent formulations as described in 1)-15) supra, which contain a stabilized or encapsulated peracid, either as an additional component or as a substitute for already specified bleach systems.

17) Detergent compositions as described supra in 1), 3), 7), 9), and 12), wherein perborate is replaced by percarbonate.

18) Detergent compositions as described supra in 1), 3), 7), 9), 12), 14), and 15), which additionally contain a manganese catalyst. The manganese catalyst for example is one of the compounds described in "Efficient manganese catalysts for low-temperature bleaching," *Nature* 369: 637-639 (1994).

19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

The Amy195 α-amylase or variant thereof may be incorporated in concentrations conventionally employed in detergents. It is at present contemplated that, in the detergent composition, the enzyme may be added in an amount corresponding to 0.00001-1.0 mg (calculated as pure enzyme protein) of Amy195 α-amylase or variant thereof per liter of wash liquor.

In another embodiment, other enzymes, such as 2,6-β-D-fructan hydrolase, can be incorporated in detergent compositions comprising the Amy195 α-amylase or variant thereof and used for removal/cleaning of biofilm present on household and/or industrial textile/laundry.

The detergent composition may for example be formulated as a hand (manual) or machine (automatic) laundry detergent composition, including a laundry additive composition suitable for pre-treatment of stained fabrics and a rinse added fabric softener composition, or be formulated as a detergent composition for use in general household hard surface cleaning operations, or be formulated for manual or automatic dishwashing operations.

In a specific aspect, the detergent composition can comprise 2,6-β-D-fructan hydrolase in addition to Amy195 α-amylase or variant thereof, and one or more other cleaning enzymes, such as a protease, a lipase, a cutinase, a carbohydrase, a cellulase, a pectinase, a mannanase, an arabinose, a galactanase, another amylolytic enzyme, a xylanase, an oxidase, a laccase, and/or a peroxidase, and/or combinations thereof.

In general the properties of the chosen enzyme(s) should be compatible with the selected detergent, (e.g., pH-optimum, compatibility with other enzymatic and non-enzymatic ingredients, etc.), and the enzyme(s) should be present in effective amounts.

Proteases: Suitable proteases include those of animal, vegetable or microbial origin. Chemically modified or protein engineered mutants are included, as well as naturally processed proteins. The protease may be a serine protease or a metalloprotease, such as an alkaline microbial protease, a trypsin-like protease, or a chymotrypsin-like protease. Examples of alkaline proteases are subtilisins, especially those derived from *Bacillus*, e.g., subtilisin Novo, subtilisin Carlsberg, subtilisin 309, subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729, WO 98/20115, WO 98/20116, and WO 98/34946. Commercially available protease enzymes include but are not limited to: Alcalase®, Savinase®, Primase™, Duralase™, Esperase®, and Kannase™ (Novo Nordisk A/S); Maxatase®, Maxacal™, Maxapem™, Properase®, Purafect®, Purafect OxP™, FN2™, and FN3™ (Genencor International, Inc.).

Lipases: Suitable lipases include those of bacterial or fungal origin. Chemically modified, proteolytically modified, or protein engineered mutants are included. Examples of useful lipases include but are not limited to lipases from *Humicola* (synonym *Thermomyces*), e.g., from *H. lanuginosa* (*T. lanuginosus*) (see e.g., EP 258068 and EP 305216), from *H. insolens* (see e.g., WO 96/13580); a *Pseudomonas lipase* (e.g., from *P. alcaligenes* or *P. pseudoalcaligenes*; see, e.g., EP 218 272), *P. cepacia* (see e.g., EP 331 376), *P. stutzeri* (see e.g., GB 1,372,034), *P. fluorescens*, *Pseudomonas* sp. strain SD 705 (see e.g., WO 95/06720 and WO 96/27002), *P. wisconsinensis* (see e.g., WO 96/12012); a *Bacillus lipase* (e.g., from *B. subtilis*; see e.g., Dartois et al. *Biochemica et Biophysica Acta*, 1131: 253-360 (1993)), *B. stearothermophilus* (see e.g., JP 64/744992), or *B. pumilus* (see e.g., WO 91/16422). Additional lipase variants contemplated for use in the formulations include those described for example in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include Lipolase® and Lipolase Ultra™ (Novo Nordisk A/S).

Polyesterase: Suitable polyesterases can be included in the composition, such as those described in, for example, WO 01/34899 and WO 01/14629.

Amylases: The compositions can be combined with other amylases, such as non-production enhanced α-amylase. These can include commercially available amylases, such as but not limited to Duramyl®, Termamyl®, Fungamyl® and BAN™ (Novo Nordisk A/S); Rapidase® and Purastar® (from Genencor International, Inc.).

Cellulases: Cellulases can be added to the compositions. Suitable cellulases include those of bacterial or fungal origin. Chemically modified or protein engineered mutants are included. Suitable cellulases include cellulases from the genera *Bacillus*, *Pseudomonas*, *Humicola*, *Fusarium*, *Thielavia*, *Acremonium*, e.g., the fungal cellulases produced from *Humicola insolens*, *Myceliophthora thermophila* and *Fusarium oxysporum* disclosed for example in U.S. Pat. Nos. 4,435, 307; 5,648,263; 5,691,178; 5,776,757; and WO 89/09259. Exemplary cellulases contemplated for use are those having color care benefit for the textile. Examples of such cellulases are cellulases described in for example EP 0495257, EP 0531372, WO 96/11262, WO 96/29397, and WO 98/08940. Other examples are cellulase variants, such as those described in WO 94/07998; WO 98/12307; WO 95/24471; PCT/DK98/00299; EP 531315; U.S. Pat. Nos. 5,457,046; 5,686,593; and 5,763,254. Commercially available cellulases include Celluzyme® and Carezyme® (Novo Nordisk A/S); Clazinase® and Puradax HA® (Genencor International, Inc.); and KAC-500(B)™ (Kao Corporation).

Peroxidases/Oxidases: Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include for example Guardzyme™ (Novo Nordisk A/S).

The detergent enzyme(s) may be included in a detergent composition by adding separate additives containing one or more enzymes, or by adding a combined additive comprising all of these enzymes. A detergent additive, i.e. a separate additive or a combined additive, can be formulated e.g., as a granulate, a liquid, a slurry, etc. Exemplary detergent additive formulations include but are not limited to granulates, in particular non-dusting granulates, liquids, in particular stabilized liquids or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (e.g., polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition may be in any convenient form, e.g., a bar, a tablet, a powder, a granule, a paste, or a liquid. A liquid detergent may be aqueous, typically containing up to about 70% water, and 0% to about 30% organic solvent. Compact detergent gels containing about 30% or less water are also contemplated. The detergent composition can optionally comprise one or more surfactants, which may be non-ionic, including semi-polar and/or anionic and/or cationic and/or zwitterionic. The surfactants can be present in a wide range, from about 0.1% to about 60% by weight.

When included therein the detergent will typically contain from about 1% to about 40% of an anionic surfactant, such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid, or soap.

When included therein, the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl-N-alkyl derivatives of glucosamine ("glucamides").

The detergent may contain 0% to about 65% of a detergent builder or complexing agent such as zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates or layered silicates (e.g., SKS-6 from Hoechst).

The detergent may comprise one or more polymers. Exemplary polymers include carboxymethylcellulose (CMC), poly (vinylpyrrolidone) (PVP), polyethylene glycol) (PEG), poly (vinyl alcohol) (PVA), poly(vinylpyridine-N-oxide), poly (vinylimidazole), polycarboxylates e.g., polyacrylates, maleic/acrylic acid copolymers), and lauryl methacrylate/acrylic acid copolymers.

The enzyme(s) of the detergent composition may be stabilized using conventional stabilizing agents, e.g., as polyol (e.g., propylene glycol or glycerol), a sugar or sugar alcohol, lactic acid, boric acid, or a boric acid derivative (e.g., an aromatic borate ester), or a phenyl boronic acid derivative (e.g., 4-formylphenyl boronic acid). The composition may be formulated as described in WO 92/19709 and WO 92/19708.

It is at present contemplated that in the detergent compositions, in particular the enzyme variants, may be added in an amount corresponding to about 0.01 to about 100 mg of enzyme protein per liter of wash liquor (e.g., about 0.05 to about 5.0 mg of enzyme protein per liter of wash liquor or 0.1 to about 1.0 mg of enzyme protein per liter of wash liquor).

4.2 Cleaning Compositions

In the detergent applications, Amy195 α-amylase and/or variant thereof are usually used in a liquid composition containing propylene glycol. The enzyme is solubilized in for example in propylene glycol by mixing in a 25% volume/volume propylene glycol solution containing 10% calcium chloride.

The Amy195 α-amylase and/or variant thereof discussed herein can be formulated in detergent compositions for use in cleaning dishes or other cleaning compositions. These can be powders, gels, or liquids. The compositions can comprise the enzyme alone, or with other amylolytic enzymes and/or with other cleaning enzymes or bleach activating enzymes, and other components common to cleaning compositions.

Thus, a dishwashing detergent composition can comprise a surfactant. The surfactant may be anionic, non-ionic, cationic, amphoteric or a mixture of these types. The detergent can contain 0% to about 90% by weight of a non-ionic surfactant, such as low- to non-foaming ethoxylated propoxylated straight-chain alcohols.

The detergent composition may contain detergent builder salts of inorganic and/or organic types. The detergent builders may be subdivided into phosphorus-containing and non-phosphorus-containing types. The detergent composition usually contains about 1% to about 90% of detergent builders. Examples of phosphorus-containing inorganic alkaline detergent builders, when present, include the water-soluble salts, especially alkali metal pyrophosphates, orthophosphates, and polyphosphates. An example of phosphorus-containing organic alkaline detergent builder, when present, includes the water-soluble salts of phosphonates. Examples of non-phosphorus-containing inorganic builders, when present, include water-soluble alkali metal carbonates, borates, and silicates, as well as the various types of water-insoluble crystalline or amorphous alumino silicates, of which zeolites are the best-known representatives.

Examples of suitable organic builders include the alkali metal; ammonium and substituted ammonium; citrates; succinates; malonates; fatty acid sulphonates; carboxymethoxy succinates; ammonium polyacetates; carboxylates; polycarboxylates; aminopolycarboxylates; polyacetyl carboxylates; and polyhydroxsulphonates.

Other suitable organic builders include the higher molecular weight polymers and co-polymers known to have builder properties, for example appropriate polyacrylic acid, polymaleic and polyacrylic/polymaleic acid copolymers, and their salts.

The cleaning composition may contain bleaching agents of the chlorine/bromine-type or the oxygen-type. Examples of inorganic chlorine/bromine-type bleaches are lithium, sodium or calcium hypochlorite, and hypobromite, as well as chlorinated trisodium phosphate. Examples of organic chlorine/bromine-type bleaches are heterocyclic N-bromo- and N-chloro-imides such as trichloroisocyanuric, tribromoisocyanuric, dibromoisocyanuric, and dichloroisocyanuric acids, and salts thereof with water-solubilizing cations such as potassium and sodium. Hydantoin compounds are also suitable.

The cleaning composition may contain oxygen bleaches, for example in the form of an inorganic persalt, optionally with a bleach precursor or as a peroxy acid compound. Typical examples of suitable peroxy bleach compounds are alkali metal perborates, both tetrahydrates and monohydrates, alkali metal percarbonates, persilicates, and perphosphates. Exemplary activator materials are TAED, and glycerol triacetate. Enzymatic bleach activation systems may also be present in the formulation, e.g., such as perborate or percarbonate, glycerol triacetate and perhydrolase (see, e.g., WO 2005/056783).

The cleaning composition may be stabilized using conventional stabilizing agents for the enzyme(s), e.g., a polyol such as, e.g., propylene glycol, a sugar or a sugar alcohol, lactic acid, boric acid, or a boric acid derivative (e.g., an aromatic borate ester).

The cleaning composition may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescers, thickeners, and perfumes.

Although the present invention(s) has been described with reference to the details below, it would be understood that various modifications can be made.

4.3 Methods of Assessing Detergent Compositions

Numerous α-amylase cleaning assays exist. Exemplary description of testing cleaning includes the following.

A "swatch" is a piece of material such as a fabric that has a stain applied thereto. The material can be, for example, fabrics made of cotton, polyester or mixtures of natural and synthetic fibers. The swatch can further be paper, such as filter paper or nitrocellulose, or a piece of a hard material such as ceramic, metal, or glass. For amylases, the stain is starch based, but can include blood, milk, ink, grass, tea, wine, spinach, gravy, chocolate egg, cheese, clay, pigment, oil, or mixtures of these compounds.

A "smaller swatch" is a section of the swatch that has been cut with a single hole punch device, or has been cut with a custom manufactured 96-hole punch device, where the pattern of the multi-hole punch is matched to standard 96-well microtiter plates, or the section has been otherwise removed from the swatch. The swatch can be of textile, paper, metal, or other suitable material. The smaller swatch can have the stain affixed either before or after it is placed into the well of a 24-, 48- or 96-well microtiter plate. The "smaller swatch" can also be made by applying a stain to a small piece of material. For example, the smaller swatch can be a stained piece of fabric ⅝" or 0.25" in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived of to deliver simultaneously swatches to any format plate, including but not limited to 24-well, 48-well, and 96-well plates. In another conceivable method, the soiled test platform can be a bead made of either metal, plastic, glass, ceramic, or other suitable material that is coated with the soil substrate. The one or more coated beads are then placed into wells of 96-, 48-, or 24-well plates or larger formats, containing suitable buffer and enzyme. In this case, supernatant can be examined for released soil either by direct absorbance measurement or after a secondary color development reaction. Analysis of the released soil might also be taken by mass spectral analysis. A further microscreening assay can be to deliver and secure a swatch, for example an indigo dyed denim, to a well of a multi-well plate, and add particles such as sand or larger particles such as for example garnet sieved to include particle 6 to 8, or 9 gauge, and agitate the plate so as to cause abrasion of the swatch by the added particles. This assay has found use in the assessment of cellulases in stone washing applications. The effectiveness of the enzyme can be judged by either color release (e.g., released indigo is dissolved in dimethylsulfoxide and absorbance at $A_{600}$ nm is measured) to the reaction buffer or by reflectance measurements of the abraded swatch.

When, for example, untreated BMI (blood/milk/ink) swatches are washed in detergent without bleach, a large portion of the ink is released even without the help of a protease. Adding a protease leads to a small increase in ink release, which can be hard to quantify over the large background. The present invention provides a treatment protocol that allows one to control the degree of fixation of a stain. As a result, it is possible to produce swatches that, for example, release varying amounts of stain when washed in the absence of the enzyme being tested. The use of fixed swatches leads to a dramatic improvement of the signal-to-noise ratio in the wash assays. Furthermore, by varying the degree of fixation, one can generate stains that give optimum results under the various cleaning conditions.

Swatches having stains of known "strength" on various types of material are commercially available (EMPA, St. Gallen, Switzerland; wfk—Testgewebe GmbH, Krefeld Germany; or Center for Test Materials, Vlaardingen, The Netherlands) and/or can be made by the practitioner (Morris and Prato, *Textile Research Journal* 52(4): 280 286 (1982)). Other test swatches include but are not limited to blood/milk/ink (BMI) stain(s) on a cotton-containing fabric, a spinach stain on a cotton-containing fabric, or grass on a cotton-containing fabric, and chocolate/milk/soot on a cotton-containing fabric.

A BMI stain can be fixed to cotton with 0.0003% to 0.3% hydrogen peroxide. Other combinations include grass or spinach fixed with 0.001% to 1% glutaraldehyde, gelatin and Coomassie stain fixed with 0.001% to 1% glutaraldehyde, or chocolate, milk and soot fixed with 0.001% to 1% glutaraldehyde.

The swatch can also be agitated during incubation with the enzyme and/or detergent formulation. Wash performance data is dependent on the orientation of the swatches in the wells (horizontal versus vertical), particularly in the 96-well plate. This would indicate that mixing was insufficient during the incubation period. Although there are a number of ways to ensure sufficient agitation during incubation, a plate holder in which the microtiter plate is sandwiched between two plates of aluminum can be constructed. This can be as simple as placing, for example, an adhesive plate sealer over the wells then clamping the two aluminum plates to the 96-well plate with any type of appropriate, commercially available clamps. It can then be mounted in a commercial incubator shaker. Setting the shaker to about 400 rpm results in very efficient mixing, while leakage or cross-contamination is efficiently prevented by the holder.

Trinitrobenzenesulfonic acid (TNBS) can be used to quantify the concentration of amino groups in the wash liquor. This can serve as a measure of the amount of protein that was removed from the swatch (see e.g., Cayot and Tainturier, *Anal. Biochem.* 249: 184-200 (1997)). However, if a detergent or an enzyme sample leads to the formation of unusually small peptide fragments (for example, from the presence of peptidases in the sample), then one will obtain a larger TNBS signal, i.e., more "noise".

Another means of measuring wash performance of blood/milk/ink or other stain is based on ink release. Proteolysis of protein on the swatches leads to the release of ink particles which can be quantified by measuring the absorbance of the wash liquor. The absorbance can be measured at any wavelength between 350 and 800 nm. The absorbance is measured at 410 nm or 620 nm. The wash liquor can also be examined to determine the wash performance on stains containing grass, spinach, gelatin or Coomassie stain. Exemplary wavelengths for these stains include 670 nm for spinach or grass and 620 nm for gelatin or Coomassie. For example, an aliquot of the wash liquor (typically 100-150 μL from a 96-well microplate, for example) is removed and placed in a cuvette or multiwell microplate. This is then placed in a spectrophotometer and the absorbance is read at an appropriate wavelength.

The system can also be used to determine an enhanced enzyme and/or detergent composition for dish washing, for example, using a blood/milk/ink stain on a suitable substrate such as cloth, plastic or ceramic.

In one aspect, the BMI stain is fixed to cotton by applying 0.3% hydrogen peroxide to the BMI/cotton swatch for 30 minutes at 25° C. or by applying 0.03% hydrogen peroxide to the BMI/cotton swatch for 30 minutes at 60° C. Smaller swatches of approximately 0.25" are cut from the BMI/cotton swatch and placed in the wells of a 96-well microtiter plate. Into each well, a known mixture of a detergent composition and an enzyme such as a variant protein is placed. After placing an adhesive plate sealer onto the top of the microtiter plate, the microtiter plate is clamped to an aluminum plate and agitated on an orbital shaker at approximately 250 rpm for about 10 to 60 minutes. At the end of this time, the supernatants are transferred to wells in a new microtiter plate and the absorbance of the ink at 620 nm is measured. This can be similarly tested with spinach stains or grass stains fixed to cotton by applying 0.01% glutaraldehyde to the spinach/cotton swatch or grass/cotton swatch for 30 minutes at 25° C. The same can be done with chocolate, milk, and/or soot stains.

EXAMPLES

Example 1

Expression in *B. subtilis*

The construct depicted in FIG. 5, was transformed into a 9 protease deleted *B. subtilis* strain (degU$^{Hy}$32, oppA, ΔspoII3501, amyE::xylRPxylAcomK—ermC, ΔaprE, ΔnprE, Δepr, ΔispA, Δbpr, Δvpr, ΔwprA, Δmpr-ybfJ, ΔnprB) (see US20050202535A1). A culture of this strain was grown in the following medium (per liter): 10 g Soytone, 75 g glucose, 7.2 g urea, 40 mM MOPS, 4 mM Tricine, 3 mM dibasic potassium phosphate, 21.4 mM KOH, 50 mM NaCl, 276 μM potassium sulfate, 528 μM magnesium chloride, 50 μM trisodium citrate dihydrate, 100 μM calcium chloride dihydrate, 14 μM ferrous sulfate heptahydrate, 5.9 μM manganese sulfate dihydrate, 5.7 μM zinc sulfate monohydrate, 2.9 μM cupric chloride dihydrate, 4.2 μM cobalt hexahydrate, 4.5 μM sodium molybdate dihydrate. For a 1 L volume, all components except for Soytone were mixed in 500 mL, sterile filtered, and added to an equal part of 2× Soytone, which had been sterilized by autoclaving. Trace metals and citrate can be made up as a 100× or 1000× stock solutions. Buffers, potassium hydroxide, sodium chloride, potassium sulfate, and magnesium chloride and trace metals can be made up as a 10× stock solutions. After all components were mixed, the pH was adjusted to 7.3. Prior to use this medium was supplemented with 20 mM calcium chloride.

The culture expressed the enzyme in various processed forms. The apparently mature form (without the signal sequence) was observed at the 69 kDa marker on a 10% SDS-PAGE gel. Two shorter forms were also present.

Figure 10:
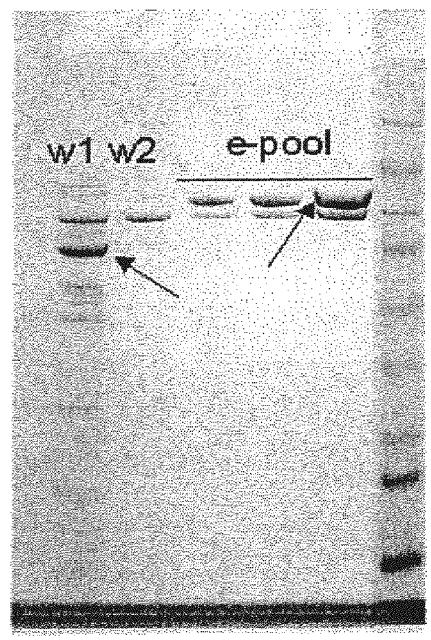
FIG. 10. Analysis of fractions from a β-cyclodextrin column, which contained Amy195 proteolytic fragments. Fractions are indicated by "w1" ("wash 1" eluted from column with 25 mM bis-tris propane, pH 8.5, 2 mM $CaCl_2$); "w2" ("wash 2" was eluted with a further aliquot of the same buffer); and "e-pool" (fractions eluted with 50 mM β-cyclodextrin in the same buffer and loaded on the gel at three different concentrations). The matrix for the β-cyclodextrin column was synthesized in-house by standard protocol from β-cyclodextrin (Sigma Aldrich Cat. No. c4767) and epoxy-activated-Sepharose-6B (GE Healthcare, N.J. Cat. No. 17-0480-01).

The Amy195 α-amylase activity was fractionated from the culture broth by treating the broth with a β-cyclodextrin-Sepharose affinity resin, collecting the resin, and washing with 25 mM bis-Tris propane buffer (pH 8.5) containing 2 mM calcium chloride (CaCl$_2$), and eluting the washed resin with the same buffer supplemented with 50 mM β-cyclodextrin. The effect of treating the culture broth with the β-cyclodextrin resin was partial removal of the 60 kDa species (to about 50%) and complete removal of the 69 kDa species from the broth. The buffer wash of the resin provided nearly pure protein of 60 kDa size; elution with buffer containing β-cyclodextrin provided the 69 kDa protein contaminated with about 25% of the 60 kDa protein. These component estimates were determined by SDS-PAGE and are depicted in FIG. 10. Enzyme content of fractions was estimated by gel densitometry with OxAm amylase (Genencor International, Inc.) serving as the protein standard. N-terminal analysis of the darkest band in the lane marked "w1" of FIG. 10 provided a sequence of "AAPGPKDATA" (SEQ ID NO: 5). Mass spectral analysis in conjunction with this N-terminal sequence identified the protein to have the sequence shown in upper case in FIG. 4 (i.e., without the signal sequence and C-terminal extension representing the starch binding motifs). These analyses indicate that this molecular fragment consists of the α-amylase domains A, B & C.

Example 2

Expression of Genetically Truncated Amy1 95 Catalytic Domain

The gene for Amy195 was truncated at three different sites to allow testing expression of the truncated forms and for testing of wash performance. Truncation was achieved by standard techniques known to those skilled in the art at amino acid residue numbers 494, 504, and 509 using the polypeptide numbering of the sequence in FIG. 4. The plasmids containing the truncated genes were transformed into a nine protease deleted *Bacillus subtilis* strain (degU$^{Hy}$32, oppA, ΔspoII3501, amyE::xylRPxylAcomK—ermC, ΔaprE, ΔnprE, Δepr, ΔispA, Δbpr, Δvpr, ΔwprA, Δmpr-ybfJ, ΔnprB). The cells were cultured in 250 mL baffled flasks containing 50 mL of rich medium supplemented with 10 or 30 mM CaCl$_2$ for 64 hours at 37° C. and shaking at 250 rpm. The culture supernatants were analyzed by SDS PAGE, and amylase content was estimated by gel densitometry.

Figure 8:
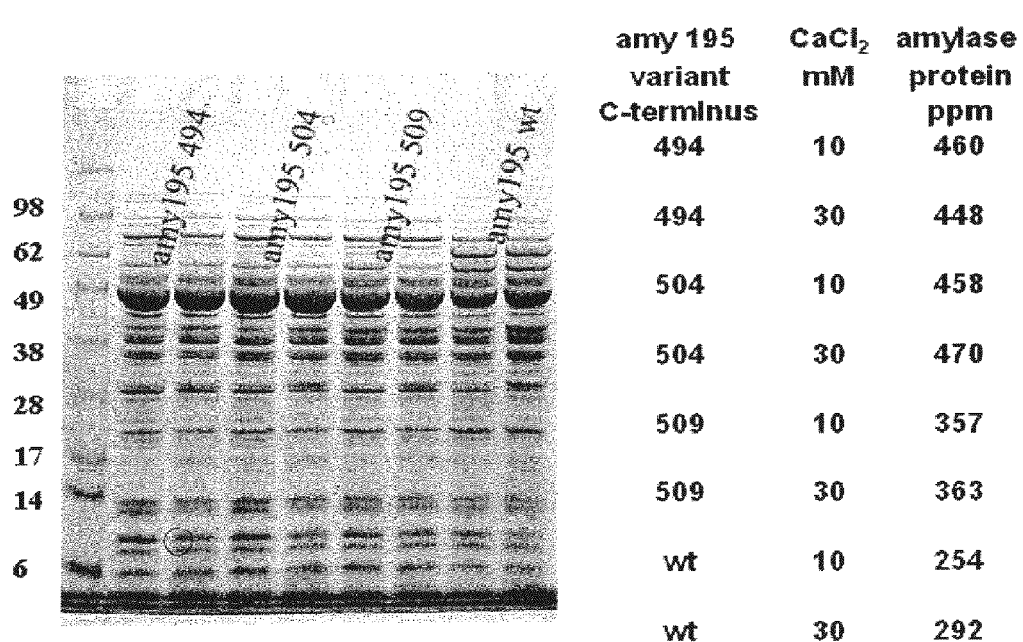
FIG. 8. SDS polyacrylamide gel was run and shows the expression of the genetically truncated Amy195 molecules. Truncations shown are C-terminally of residue 494, 504, and 509, using the numbering of FIG. 4. Expression cultures were carried out as described in Example 2 and concentration was estimated with OxAm used as the density standard.

Expression of amylase from the truncated genes was found to be about 2-fold higher than expression of the same domain from the full-length wild type gene. These results are shown in FIG. 8 and indicate that the truncated gene is advantageous for protein expression.

Example 3

Cleaning Assay

All fractions shown on the gel were analyzed further by 96-well CS28 orange dyed rice starch soil swatch applications assay. This assay was carried out in the 25 mM HEPES (pH 8.0) as well as in 25 mM CAPS (pH 10.3) buffers.

Figure 6:
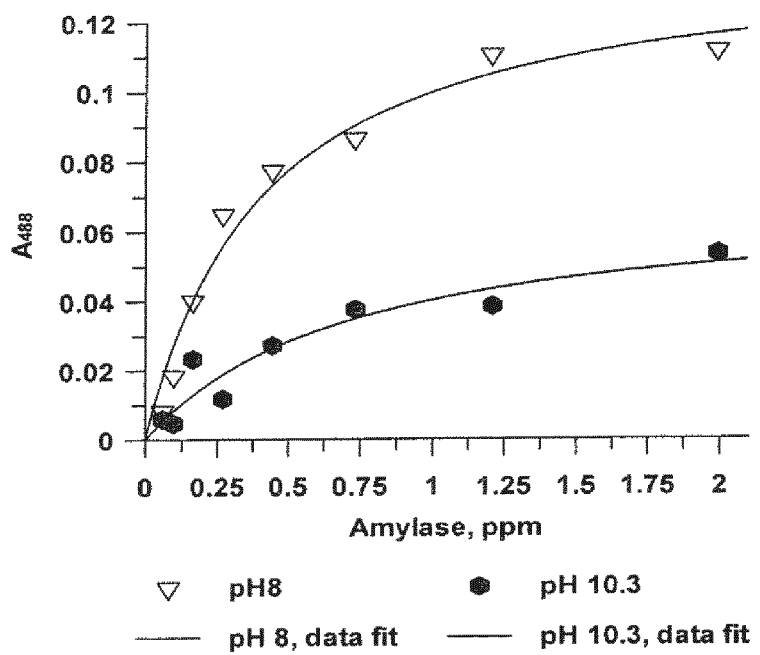
FIG. 6. Depicts the results for performance assay for the Amy195 enzyme, as a function of pH and protein concentration. The fraction assayed is that indicated as e-pool on FIG. 10. The assay was carried out in a 96-well plate assay. One-quarter inch textile swatches soiled with colored rice starch (Testfabrics Inc., CS28 colored rice starch) were placed in each well. Buffer: 25 mM HEPES pH 8.0 or 25 mM CAPS pH 10.3 was added to each well. The plate was pre-incubated at 40° C. The reaction was started by the addition of Amy195 enzyme to a final concentration of 0 ppm to 2 ppm. The plate was incubated at 40° C. for 10 minutes with shaking at 750 rpm in an Eppendorf Thermomix apparatus. After this incubation supernatant fluid was moved to a new 96-well plate and absorbance at 488 nm was read in a Molecular Devices plate reader, model Spectra Max 190. The data was plotted with the aid of the software package GRAFIT from Erithicus software. The data points were fitted with the Langmuir isotherm fitting algorithm, which takes the same form as the Michaelis-Menten fitting algorithm, which is available with the software. Every Amy195 protein expressed contains the signal peptide from LAT, but this is clipped off during the secretion process and is not present in the mature Amy195 protein.
Figure 7:
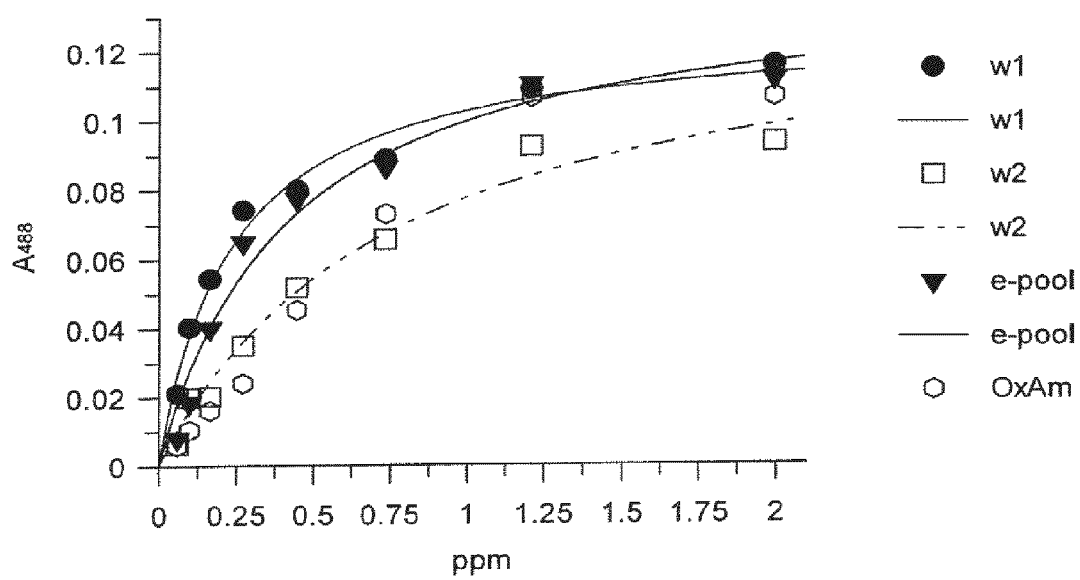
FIG. 7. Performance assay of all proteolytic fragments as shown in FIG. 10. The assay was carried out and plotted as described in Example 3 and the legend of FIG. 6 at pH 8. The data shows that all fractions perform equal to or better than OxAm (Genencor International, Inc.).

Cleaning performance of all Amy195 species isolated in Example 1 was tested in a simulated laundry assay as a function amylase concentration. Results for fraction "e-pool" of FIG. 10 are shown in FIG. 6. Performance was judged by the amount of color released into the supernatant fluid and measured using a spectrophotometer at 488 nm. For additional information on the assay, see U.S. Pat. No. 7,122,334. The enzyme was highly efficient at pH 8.0, but also showed surprising stain removal at pH 10.3. All major protein bands of each lane of the protein gel (FIG. 10) showed cleaning with the band of lane "w1" giving the best performance. All cleaning activities are shown in FIG. 7 under the pH 8.0 conditions. The truncated form ending at amino acid residue 492 of FIG. 4 demonstrated better performance (see FIG. 7, "●") than the form retaining one starch binding domain (see FIG. 7, "□").

Results from this assay show that Amyl 95 α-amylase is highly efficient in removing stains from textile swatches.

Example 4

Wash Performance of the Genetically Truncated Gene Product

Figure 9:
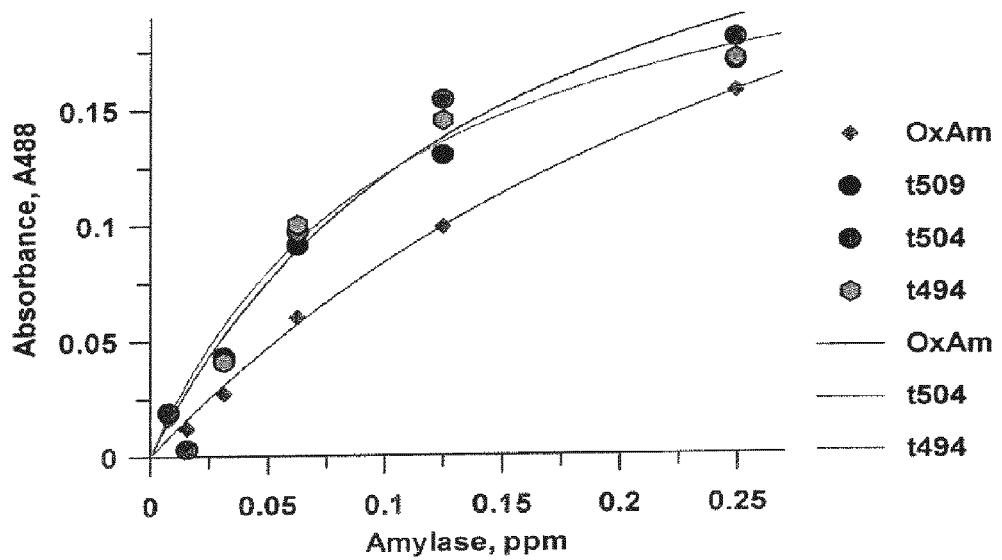
FIG. 9. Application performance of genetically truncated Amy195 amylase variants. Performance assays were conducted using culture supernatant without further purification. Assay procedure and data plotting is described in Example 3 and the legend of FIG. 6, at pH 8.0. The data shows that all truncated molecules performed better than OxAm.

The truncated gene products obtained in Example 2 above were tested for wash performance in the same manner as described for the proteolytic fragments in Example 3 above. CS28 rice swatches were incubated with a range of Amy195 catalytic fragment concentrations. Wash performance was judged by color released into the supernatant and measured at 488 nm. All three genetically truncated gene fragments showed good wash performance as is shown in FIG. 9.

This swatch assay can be modified in several ways for different purposes. The 96-well assay is highly suitable as a high-throughput cleaning assay by measuring the supernatant after incubation of enzyme with swatches, while for example, a 24-well plate with swatches to fit in the wells can be used to wash larger swatches for which reflectance can be measured as known in the art. The two measurements, supernatant absorbance and swatch reflectance, showed nearly perfect correlation.

The correlation of reflectance of the washed swatch with the absorbance of supernatant was high; the coefficient of determination, $r^2$, had a value of 0.99. The assay can, in principle, be scaled to a 384-well plate. The assay can be carried out with any soiled swatch and in addition to the CS28 swatch, CS26, CS27, and CS29 swatches can be tested as well (e.g., corn starch, potato starch, tapioca starch, respectively; Testfabrics, Inc., West Pittiston, Pa.) to demonstrate the efficacy of the measurement as described in Example 3. The assay may also be used with detergent compositions and conducted at different temperatures and at different pH values. These assays were adapted from U.S. Pat. No. 7,122,334.

All references cited above, are herein incorporated by reference in their entirety for all purposes.

What is claimed is:

1. A method of washing dishes comprising applying a manual or automatic dishwashing detergent composition comprising a polypeptide consisting essentially of residues 30-492 of SEQ ID NO:4, or having at least 98% amino acid sequence identity, thereto, to a dish in need thereof.

* * * * *